(12) United States Patent
Talbot et al.

(10) Patent No.: US 6,801,420 B2
(45) Date of Patent: Oct. 5, 2004

(54) SELECTIVE POTTING FOR CONTROLLED FAILURE AND ELECTRONIC DEVICES EMPLOYING THE SAME

(75) Inventors: Cary D. Talbot, Santa Clarita, CA (US); Sheldon B. Moberg, Granada Hills, CA (US); James D. Causey, III, Simi Valley, CA (US); Jay A. Yonemoto, Arcadia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 363 days.

(21) Appl. No.: 10/013,943

(22) Filed: Dec. 8, 2001

(65) Prior Publication Data

US 2002/0171297 A1 Nov. 21, 2002

Related U.S. Application Data

(63) Continuation-in-part of application No. 09/838,699, filed on Apr. 19, 2001, now abandoned.

(51) Int. Cl.[7] .............................................. H02H 3/00
(52) U.S. Cl. ........................... 361/100; 361/18; 361/23; 361/706; 361/752
(58) Field of Search .............................. 361/1, 18, 23, 361/100, 115, 706, 752

(56) References Cited

U.S. PATENT DOCUMENTS

| | | | | |
|---|---|---|---|---|
| 3,558,987 A | * | 1/1971 | Lewis ......................... | 361/103 |
| 4,224,565 A | | 9/1980 | Sosniak et al. ................ | 324/65 |
| 4,698,582 A | | 10/1987 | Braun et al. ................. | 323/285 |
| 5,207,666 A | | 5/1993 | Idriss et al. ............... | 604/891.1 |
| 5,381,304 A | * | 1/1995 | Theroux et al. ............ | 361/706 |
| 5,592,121 A | | 1/1997 | Jung et al. .................. | 327/541 |
| 5,699,231 A | | 12/1997 | ElHatem et al. ............ | 361/752 |
| 5,790,108 A | | 8/1998 | Salcudean et al. .......... | 345/184 |
| 5,814,090 A | * | 9/1998 | Latterell et al. .............. | 607/36 |
| 5,821,715 A | | 10/1998 | Plutowski et al. .......... | 328/472 |
| 6,265,851 B1 | | 7/2001 | Brien et al. ................. | 320/112 |
| 6,286,566 B1 | | 9/2001 | Cline et al. ................... | 141/83 |

FOREIGN PATENT DOCUMENTS

EP          0 401 940          10/1986          ............ H01G/1/10

OTHER PUBLICATIONS

PCT International Search Report as issued in International Application No. PCT/US02/39086, Mailing date Jun. 4, 2003.

* cited by examiner

*Primary Examiner*—Stephen W. Jackson
(74) *Attorney, Agent, or Firm*—Foley & Lardner LLP

(57) ABSTRACT

A selectively protected electrical system includes or operates with a power source, a load, a power driver circuit for controllably transferring power from the power source to the load, the power driver circuit being encapsulated in a potting material, and a controller for enabling and disabling the power driver circuit, the controller being un-encapsulated by the potting material. If a contaminant induced electrical fault occurs in the selectively protected electrical system, the electrical fault is more likely to occur in the un-encapsulated controller, such that the selectively protected electrical system is disabled. The contaminant is inhibited from contacting and inducing an electrical fault in the power driver circuit, thus providing for a controlled failure of the selectively protected electrical system.

62 Claims, 13 Drawing Sheets

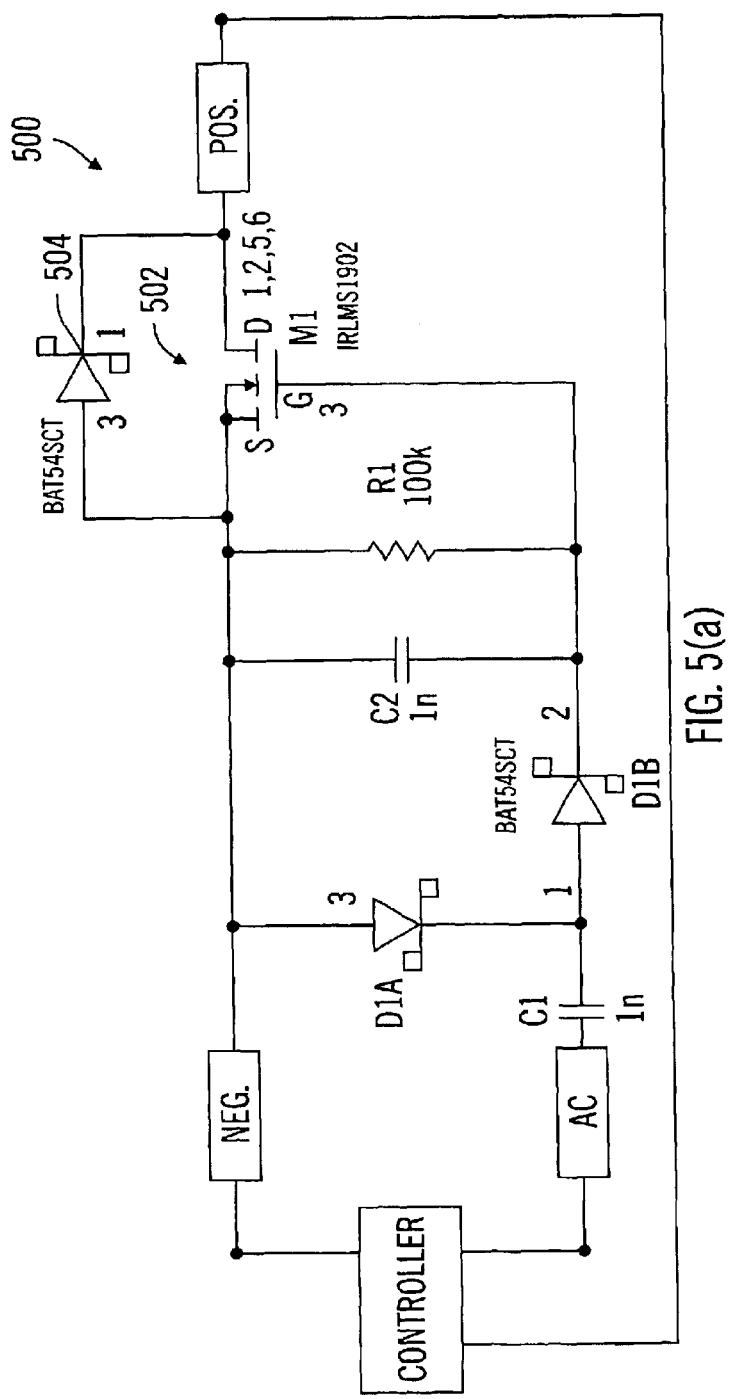
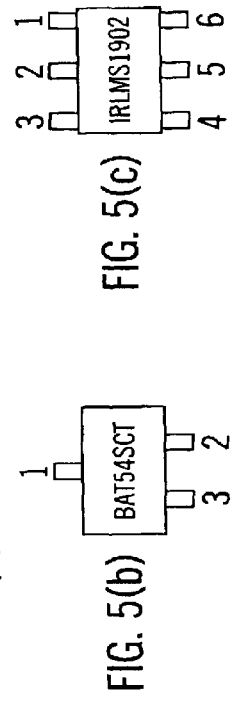
FIG. 5(a)
FIG. 5(b)
FIG. 5(c)

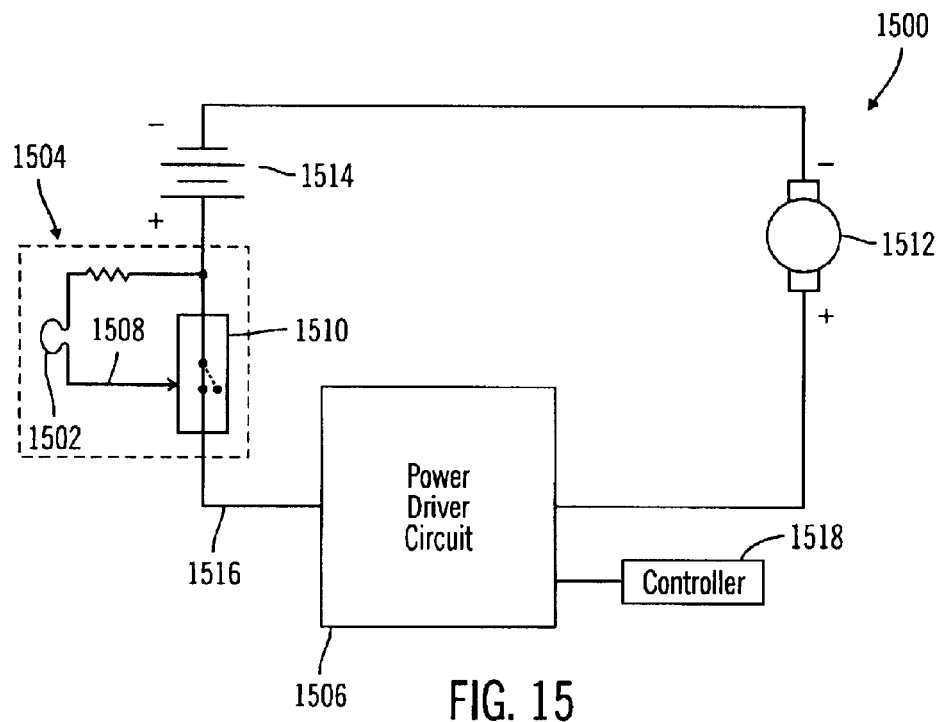
FIG. 15
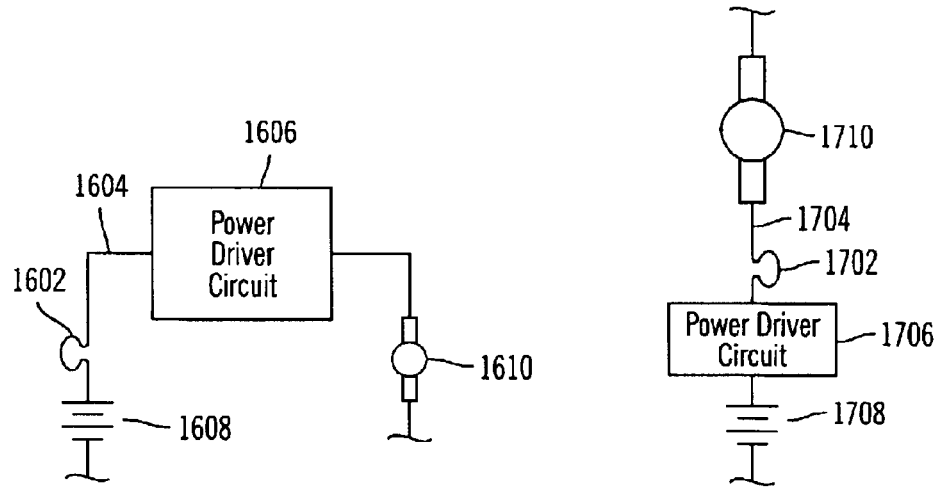
FIG. 16
FIG. 17

SELECTIVE POTTING FOR CONTROLLED FAILURE AND ELECTRONIC DEVICES EMPLOYING THE SAME

RELATED APPLICATIONS

The present disclosure relates to and is a continuation-in-part of U.S. patent application Ser. No. 09/838,699, titled, "Direct Current Motor Safety Circuits for Fluid Delivery Systems," filed Apr. 19, 2001 now abandoned, which is incorporated herein by reference. Priority of the earlier filing date of the above-referenced application is claimed herein.

FIELD OF THE INVENTION

This invention relates to a system and method for controlled failure in electronic devices and, in particular embodiments, to selective potting for controlling failures in defined operations such as controlled failure of a pump driver for delivery of medication or drugs to a patient.

BACKGROUND OF THE INVENTION

There are many types of electronic devices (medical devices, sensing devices, and the like) that can fail due to moisture or other environmental contaminants coming into contact with the device electronics. A common mechanism is the addition of water to contaminants that combine to form ionic solutions that are conductive and may lead to failure of the electronic device. The failure of such devices may have, in some cases, serious consequences for users of systems which contain the devices. For example, if the device is used in a medical system such as an infusion pump for the delivery of medications/drugs, a failure of the device may lead to accidental over-delivery of the medications/drugs, possibly resulting in injury or death.

One common manner of protecting electrical and electronic components and circuits in such systems against contact with moisture or other environmental contaminants involves covering the electronics of such systems with potting materials that are resistant to contaminants such as moisture. One drawback of this method is that known potting materials can fail to protect the electrical system against long-term contaminant penetration. For example, over time, moisture may diffuse through the potting material, where the penetrated moisture will likely detrimentally affect the performance of the electrical system and may lead to unpredictable and possibly dangerous system failures. Also, the potting materials may degrade, separate or pull away from and expose the electrical and electronic components and circuits, which may reduce the effectiveness of the protection by exposing the various components and system to contaminants.

The contaminant may pass by or diffuse through the potting material that covers particular electrical or electronic components which may be "critical" because they affect a critical operation of a system (i.e., the failure of which may have serious consequences). Such critical operations may include, for example, electronics for controlling a motor that, for example drives an infusion pump for delivering a medication to a patient. A resulting failure of critical electrical or electronic components due to contact with a contaminant may have serious consequences such as those described above.

As discussed above, conventional drug delivery systems such as infusion pumps are examples of systems wherein a failure of the systems' electronics may have serious consequences. An infusion pump system can include electronic control circuits and electronic power driver circuits, as well as other circuitry. The control electronics can control the power driver circuit to drive a motor which, in turn, drives the infusion pump. One such drug delivery system is used to deliver insulin over a period of time and utilizes a variety of motor technologies to drive an infusion pump. Typical motor technologies include direct current (DC) motors, stepper motors, or solenoid motors. Each motor type has various advantages and disadvantages related to cost, reliability, performance, weight, and safety.

In drug delivery using infusion pumps, the accuracy of medication delivery can be critical (such as for insulin, HIV drugs or the like), since minor differences in medication quantity can dramatically affect the health of the patient. Thus, safeguards must be designed into the delivery system to protect the patient from over or under delivery of medication. For example, in the case where insulin is administered via an infusion pump to a diabetic patient, excessive drug delivery could cause complications due to hypoglycemia, and could possibly even result in death. Therefore, controlled delivery with safeguards against over-delivery of medications is required for drug delivery systems when over-delivery could result in complications, permanent damage, or death of the patient.

In conventional systems, these safeguards against over-delivery have been incorporated into the drive systems of infusion pumps in varying ways. For example, the motor control electronics utilize cross checks, encoder counts, motor current consumption, occlusion detection, or the like, as a form of feedback to guard against over or under delivery of medication. However, one drawback to this approach can occur if the control electronics in a DC motor driven infusion pump were to fail, such that a direct short occurs from the power source to a DC motor in the infusion pump. For example, in one failure mode, it would be possible for the DC motor to drive continuously for an excessive period of time, for example, until the power source was depleted or removed, or until the short was removed. This condition is commonly referred to as motor "run away", and could result in all of the medication contained in the infusion pump being infused immediately over too short a period of time resulting in injury or death to the patient.

To avoid this drawback, some infusion pump manufactures have avoided the use of DC motors and have instead utilized solenoid or stepper motor technologies. With these motor types, any short in the control electronics, would only result in, at most, a single motor step. Therefore, motor "run away" would not occur. Thus, this minimizes the risk of a "run away" failure. However, a drawback to the use of solenoid or stepper motor technologies is they generally have a less efficient performance with regard to battery energy, tend to cost more as compared to the DC motors, and may only be capable of running in one direction (i.e. not reversible).

SUMMARY OF THE DISCLOSURE

It is an object of embodiments of the present invention to provide a system and method of selectively protecting electrical and/or electronic components or circuits within a particular system to provide for controlling a system failure in a manner where the likelihood of a failure that causes damage or an undesired (or dangerous) condition is reduced.

Embodiments of the invention employ a selective potting system and method for this purpose. According to embodiments of the present invention, critical electrical and electronic components and/or circuits of a system are encapsulated in a potting material. Non-critical components of the system may remain un-encapsulated. The un-encapsulated non-critical components are selected to be components that are likely to contact a contaminant and fail in a predictable or desired manner. Thus, the failure of the non-critical components may disable the protected system in the event that the system becomes contaminated. Accordingly, the system may be disabled before the critical electrical and electronic components and/or circuits can be contacted by the contaminant, which could then fail in a manner that would be undesirable, dangerous, or damaging to the system. It is the purpose of the invention to control the failure of a system by deliberately exposing components of the system to contaminant failure while protecting other system components. Embodiments of the invention may be employed in various electrical and electronic systems, including control systems, guidance systems, navigation systems, fusing systems, acquisition and tracking systems, command systems, sensor systems, power systems, communication systems, computer systems, network systems, processors, or the like, and particularly, automotive and aircraft control systems, sensors and other monitoring devices, military systems for ordinance delivery, medical devices, computers, personal digital assistants (PDAs),and the like.

One embodiment of the present invention is employed in a fluid delivery system including an infusion device for delivering a medication/drug/fluid. An example infusion device is driven by a DC motor. The DC motor may also include safety enhancements such as safety circuits, which obviate, for practical purposes, the above mentioned limitations.

According to an embodiment of the invention, a selectively protected electrical system includes or operates with a power source, a load, a power driver circuit for controllably transferring power from the power source to the load, the power driver circuit being encapsulated in a potting material, and a controller for enabling and disabling the power driver circuit, the controller being un-encapsulated by the potting material. If a contaminant induced electrical fault occurs in the selectively protected electrical system, the electrical fault is more likely to occur in the un-encapsulated controller, such that the selectively protected electrical system is disabled. The contaminant is thus inhibited from inducing an electrical fault in the power driver circuit. Other embodiments may employ other types of drive motor circuits having critical and non-critical components. Selective protection in accordance with embodiments of the invention may be used in combination with embodiments of the safety circuit system or in the alternative.

According to other embodiments of the invention, a safety circuit system for a DC driven device for use with a fluid delivery system includes a first voltage potential DC power line, a second voltage potential DC power line, a controller and a safety circuit. The first voltage potential DC power line is coupled to provide a first voltage potential to the DC driven device, and the second voltage potential DC power line is coupled to provide a second voltage potential to the DC driven device such that the second voltage potential is different relative to the first potential. The controller controls at least the first voltage potential on the first voltage potential DC power line. The safety circuit has an enable state and a disable state, in which the default state is the disable state. The safety circuit is coupled to the controller, and the controller controls the safety circuit to place the safety circuit in the enable state independently of controlling the first voltage potential on the first voltage potential DC power line. The safety circuit is operatively coupled to at least one of the first and second voltage potential DC power lines to inhibit DC flow and operation of the DC driven device when the safety circuit is in the disable state and to permit DC flow and operation of the DC driven device when the safety circuit is in the enable state such that the operation of the DC driven device will occur when the safety circuit is in the enable state. In preferred embodiments, the DC driven device is a DC motor in an infusion pump. Alternatively, the DC driven device is a gas generator in an infusion pump. In preferred embodiments, the safety circuit is controlled by an AC signal from the controller such that the safety circuit is enabled by the AC signal to permit DC flow and enable the forward motion of the DC motor while the AC signal is provided by the controller.

In embodiments that utilize a DC motor with a safety circuit, the safety circuit being in the disable state operates to inhibit the forward motion of the DC motor when the difference of the first voltage potential relative to second voltage potential is positive. In addition, the safety circuit being in the disable state is inoperative to inhibit a reverse motion of the DC motor when the difference of the first voltage potential relative to second voltage potential is negative. Alternatively, or in addition to, the safety circuit being in the disable state operates to inhibit a reverse motion of the DC motor when the difference of the first voltage potential relative to second voltage potential is negative. In addition, the safety circuit being in the disable state operates to inhibit the forward motion of the DC motor when the difference of the first voltage potential relative to second voltage potential is negative. Further, the safety circuit being in the disable state is inoperative to inhibit a reverse motion of the DC motor when the difference of the first voltage potential relative to second voltage potential is positive. Alternatively, the safety circuit being in the disable state operates to inhibit a reverse motion of the DC motor when the difference of the first voltage potential relative to second voltage potential is positive.

Preferred embodiments are directed to an infusion pump, in which the safety circuit is used to prevent operation of the DC motor during a controller failure to prevent accidental delivery of excess fluid. In particular embodiments, the safety circuit is integral with the DC motor. In other embodiments, the safety circuit is co-located with the controller.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several Figures.

FIG. 5(a) is a schematic diagram of a safety circuit that is a further variation of the embodiment shown in FIG. 3.

FIG. 5(b) is a top view of a pin out diagram for a component used in the circuit shown in FIG. 5(a).

FIG. 5(c) is a top view of a pin out diagram for another component used in the circuit shown in FIG. 5(a).

FIG. 15 illustrates a simplified schematic circuit diagram of a dissolvable switch or circuit used to shut-off power to a power driver circuit in accordance with an embodiment of the present invention.

FIG. 16 illustrates a simplified partial schematic circuit diagram of a dissolvable fuse, switch, or circuit used with the power driver circuit in accordance with an embodiment of the present invention.

FIG. 17 illustrates a simplified partial schematic circuit diagram of a dissolvable fuse, switch, or circuit used with a DC motor, or the like, in accordance with an embodiment of the present invention.

DETAILED DESCRIPTION OF THE PREFERRED EMBODIMENTS

Figure 1:
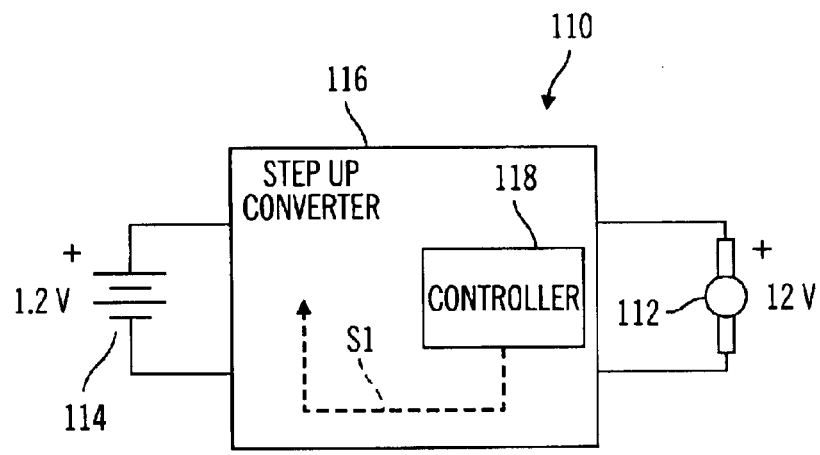
FIG. 1 is a schematic diagram of a safety circuit in accordance with a first embodiment of the present invention.

As shown in the drawings for purposes of illustration, the invention is embodied in a system and method for selectively encapsulating or potting particular electrical and/or electronic components and/or circuits which provides for controlling a system failure in a manner where the likelihood of a critical failure is reduced. Encapsulating or potting particular electrical and/or electronic components and/or circuits may include covering one or more electrical and/or electronic components and/or circuits with a potting material on one or more sides. It may include partially or fully covering the electrical and/or electronic components and/or circuits. Embodiments of the present invention selectively encapsulate in a potting material a critical portion or portions of a particular electrical or electronic system. A critical portion of a system may contain critical components for performing a critical operation. Critical components of an electrical or electronic system include components that, failing, may cause undesirable, dangerous, and/or damaging operation of the system. Critical portions of a particular system may include, for example, electronic circuits or circuit components for controlling a load. A load may include a motor, an actuator, a hydraulic system, a pneumatic system, a pump, a compressor, a turbine, a generator, a valve, and the like. A load may perform a critical operation such as automobile braking. Critical portions of a particular system may further include electronic circuits or circuit components employed in an avionics system for critical operations such as controlling, for example, an aileron, rudder, or elevator used to control or guide an aircraft or missile. Further examples include electronic circuits or circuit components used in medical systems for controlling devices such as infusion pumps for performing critical operations such as medication/drug delivery, sensors and monitors for critical operations such as sensing or monitoring a patient's condition, and pacemakers for critical operations such as stimulating or controlling a patient's heart contraction rate. Critical components may be found in other devices such as control systems, guidance systems, navigation systems, fusing systems, acquisition and tracking systems, command systems, sensor systems, power systems, communication systems, computer systems, network systems, processors, or the like, and particularly, automotive and aircraft control systems, sensors and other monitoring devices, military systems for ordinance delivery, medical devices, computers, personal digital assistants (PDAs), and the like, where controlled failure or desired or predicable disablement is desired or required. Non-critical components of an electrical or electronic system include components that, failing, may cause disablement or a predictable (or desired) failure of the device or system, but are not likely to cause undesirable operation of the electrical or electronic system.

Example embodiments of the present invention include a power supply, a power driver circuit, a controller, and a load. The power supply includes one or more batteries, generators, alternating current (AC) or direct current (DC) supplies, electrical power sources, and the like. The power supply provides power to the power driver circuit. The power driver circuit is connected to the load, and the load is connected to the power supply completing the circuit. The controller provides signals to the power driver circuit to cause the power driver circuit to connect or disconnect power from the power supply to the load.

Preferred embodiments of the present invention are described in relation to a fluid delivery system for the delivery of a medication/drug. However, other embodiments may be employed in other electrical and electronic systems having critical and non-critical components.

One embodiment is described in relation to a fluid delivery system using an infusion pump driven by a DC motor. In one embodiment, the DC motor is driven by a power driver circuit comprising an H-bridge configuration of switching elements. Other embodiments may employ other suitable power driver circuits, such as those described below. The power driver circuit is controlled by a controller including control electronics and/or at least one microprocessor. One or more batteries supply power to the power driver circuit. The power diver circuit connects or disconnects the power to the DC motor when commanded by the controller.

In one embodiment, the power driver circuit is a critical component and the controller is a non-critical component. The power driver circuit is selectively potted and the controller is left un-potted. Thus, if the system comes in contact with a contaminant, an ionic contaminant for example, the controller is likely to fail and disable the system before the power driver circuit can come in contact with the contaminant, thus reducing the possibility of inadvertently powering the load, which in particular embodiments is a motor.

In other embodiments, the power driver circuit is a critical component and the power supply is a non-critical component. The power driver circuit is selectively potted and the power supply is left un-potted. Thus, if the system comes in contact with a contaminant, the power supply is likely to fail and disable the system before the power driver circuit can come in contact with the contaminant, thus reducing the possibility of inadvertently powering the load.

In particular embodiments, leads, traces, or the like from each pole of the power supply are left exposed in close proximity to each other so that a contaminant can cause a short-circuit between the leads, thus removing or diminishing power to the power driver circuit and/or the DC motor or other loads. In alternative embodiments, a fuse is included between the power supply and one or more of the exposed leads. When the two or more leads from the power supply are shorted together due to a contaminant, the fuse is blown thus removing power. The fuse is protected from contamination so that the contamination cannot short across the fuse.

In some embodiments, a safety circuit for the DC motor, which inhibits accidental over delivery of medications/drugs is employed, alternatively or in addition to, selective potting is used to protect selected components of the fluid delivery system from contamination.

In further embodiments, one or more dissolvable circuit elements, such as fuses, may be employed, alternatively or in addition to, selective potting. The one or more dissolvable circuit elements may dissolve when contacted by a contaminant and, for example, open a circuit path. Once one or more of the dissolvable circuit elements dissolve, the system may be disabled before the power driver circuit comes in contact with the contaminant. In further embodiments, the one or more dissolvable circuit elements dissolve in a manner that reduces the resistance of the electrical path that it covers and causes the circuit path to fully close and act as a short.

Yet other embodiments of the present invention may employ one or more contaminant sensing elements, such as humidity sensors, alternatively or in addition to, selective potting. The one or more contaminant sensing elements may be left un-encapsulated by potting material such that a contaminant may be sensed by the contaminant sensing elements before the contaminant may contact other portions of the electrical system. In one embodiment, the one or more contaminant sensing elements may communicate with a controller or other device operative to produce a user-perceptible signal, such as an audible alarm, vibration, shock, optical indication, a display, transmitting a signal to another device, or the like, to alert a user that a contaminant has been sensed within the system. In another embodiment, the one or more contaminant sensing elements may be operative to safely shut down the electrical system once a contaminant has been sensed.

Although embodiments of the invention are described in relation to a medical system for controlling an infusion pump, one skilled in the art will understand that embodiments of the present invention may be used in many other electrical or electronic systems as well to avoid malfunctions of electronic circuits and/or false readings of a sensor or monitor. For example, the sensor systems might be used with blood glucose meters, continuous glucose monitors, heart rate monitors, oxygen sensors, or the like. The sensors may be used to monitor or adjust therapies. Controlled failure and/or disablement of the sensors may be required to avoid ill-informed therapy adjustments that might lead to adverse results for a patient. Also, embodiments of the present invention may be employed in control systems, guidance systems, navigation systems, fusing systems, acquisition and tracking systems, command systems, sensor systems, power systems, communication systems, computer systems, network systems, processors, or the like, and particularly, automotive and aircraft control systems, sensors and other monitoring devices, military systems for ordinance delivery, medical devices, computers, personal digital assistants (PDAs),and the like. In fact, embodiments of the present invention may be employed in any electrical or electronic system wherein it is advantageous to provide for a controlled failure of the system.

As discussed above, embodiments of the present invention may be employed in a fluid delivery system including an infusion drive mechanism for delivering a medication, drugs, and/or fluid. Embodiments of the present invention may further employ, in addition to selective potting, a safety circuit employed to inhibit accidental over-delivery of medications/drugs due to DC motor control circuit failures.

Some embodiments of safety circuits are first described so that a later description of embodiments of the selective potting system and method may be fully understood with regard to the circuits described therein. However, it should be understood that embodiments of the invention might be practiced or used without or in addition to the safety circuits described below. The safety circuits are being merely provided as one example to demonstrate an improvement that utilizes selective potting, and the present invention should not be limited to the selective potting of these particular circuits described below.

In preferred embodiments of these safety circuits, a controller provides a signal to a safety circuit, in addition to providing power for the DC motor in an infusion pump, that enables the DC motor to operate only when an enabling signal is provided to the safety circuit. However, it will be recognized that further embodiments of the invention may be used to inhibit motor operation with additional signals or by controlling other aspects of the infusion pump. The safety circuits are primarily adapted for use in infusion pumps that deliver medication (or fluid) to subcutaneous human tissue. However, still further embodiments may be used with infusion pumps for other types of tissue, such as muscle, lymph, organ tissue, veins, arteries or the like, and used in animal tissue. The infusion pumps are also primarily for external use; however, alternative embodiments may be implanted in the body of a patient. The fluid delivery systems are also primarily for delivery of medication, drugs and/or fluids to a patient; however other embodiments may be used with other fluid delivery systems that require a high degree of confidence that a DC motor "run away" will not occur, such as in certain manufacturing techniques or the like. Preferred embodiments are directed to safety circuits for DC motors. However, alternative embodiments may be used with other DC driven devices, such as a DC activated gas generator in an infusion pump or the like.

Preferred embodiments are directed to circuits and methods for using DC motor technology in fluid delivery systems with additional safety circuits to prevent DC motor "run away". Use of this technology obviates the need for the use of comparatively less efficient and more expensive stepper motor and solenoid motors. All of the illustrated embodiments include a DC motor and some DC motor control electronics, although other components or DC driven devices may be used. The control electronics may be relatively simple, such as only including the capability of turning the DC motor on and off by supplying power for the duration of a key press, or may be more complex using microprocessors having multiple programmable control profiles utilizing feedback from an encoder, driving current or the like.

FIG. 1 illustrates a safety circuit 110 in accordance with a first embodiment of the present invention. In this embodiment, a DC motor 112 is configured to have a nominal voltage winding that is significantly higher then a supply voltage from a battery 114. To generate a sufficient voltage to operate the DC motor 112, the safety circuit 110 utilizes a DC-DC step up converter 116 (or similar), that includes an integral controller 118, between the battery 114 and the DC motor 112 to drive the DC motor 112 at its rated voltage (see FIG. 1). Generally, when a DC motor is supplied with the rated voltage (and also assuming there is sufficient current available), the DC motor will provide a known torque. If, for example, the supply voltage is halved, then the DC motor will only provide approximately half the full voltage output torque. However, a two, or more, times DC-DC step up converter could be utilized between the battery and the DC motor to provide the rated voltage to the DC motor. Thus, to provide a safety circuit, the nominal motor voltage winding is selected to be some large multiple of the supply voltage from the battery, such as ten times, or the like, higher then the supply voltage from the battery. Therefore, if the battery 114 is shorted directly to the DC motor 112 (i.e., as when there is an control electronics 118 failure and/or DC-DC step up converter 116), the DC motor's 112 output torque would only be approximately 1/10 of the rated value.

Generally, if the friction in the complete drive system (e.g., drive gears, shaft, or the like) is approximately 1/10 of the nominal rated value, the DC motor 112 will not have enough available torque to drive the system and cause a "run away" condition. To drive the DC motor 112 with sufficient torque, a DC-DC step up converter 116 would be required with approximately a ten times step up capability. For additional safety, alternative embodiments of the safety circuit 10 would include the DC-DC step up converter 116 such that it would only be enabled by an additional internal signal S1 (shown in dashed lines) from the integral control electronics 118. Thus, if the control electronics 118 were to fail, there would be no enable signal to provide the required step up voltage to drive the DC motor 12 in a "run away" condition. Alternative embodiments may utilize different battery supply voltages to rated nominal motor voltages ratios, with the choice being based on system friction, tolerance for movement, cost of control electronics and DC motors, or the like. In further alternatives, the control electronics 118 may be separated from the DC-DC step up converter 116 and provided as a discrete element that is placed before or after the DC-DC step up converter 116.

Figure 2:
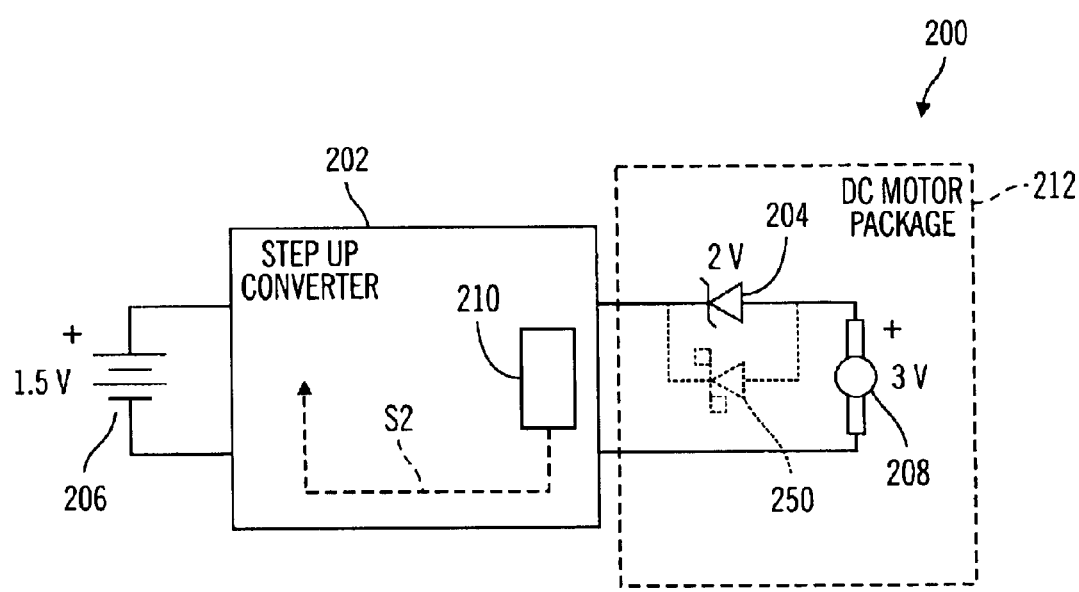
FIG. 2 is an illustrative schematic diagram of a safety circuit in accordance with a second embodiment of the present invention.

FIG. 2 illustrates a safety circuit 200 in accordance with a second embodiment of the present invention that builds upon the embodiment shown in FIG. 1. The safety circuit 200 utilizes a DC-DC step up converter 202 (that includes integral control electronics 210) and a Zener diode 204. The DC-DC step up converter 202 converts the supply voltage from the battery 206 to a value corresponding to the sum of the rated motor winding voltage of the DC motor 208 and the Zener diode 204. For instance, if the DC motor 208 has 3.0 volt motor winding and the Zener diode 204 has a breakdown voltage of 2.0 volts, the DC-DC step up converter 202 must provide 5.0 volts to facilitate operation of the DC motor 208 at its nominal rated voltage, if it is desired to drive the DC motor 208 at the rated voltage. Thus, in this example, when the supply voltage from the battery 206 is stepped up to 5 volts as a positive voltage potential, 2 volts are lost through the Zener diode 204 and 3 volts are provided for operation of the DC motor 208. In the reverse direction (i.e. a negative voltage potential), the DC-DC step up converter 202 only needs to step up the 1.5 volts supply voltage from the battery 206 to 3 volts, since there is little loss through the Zener diode 204 in the reverse direction. In an alternative embodiment, a Schottky diode 250 (shown in dashed lines in FIG. 2) may be placed in parallel with the Zener diode 204 to facilitate a low and predictable voltage drop in the reverse direction (i.e., negative voltage potential). Alternatively, if a higher speed rewind (e.g., more torque) is desired and/or required, the DC-DC step up converter 202 can still be stepped up to the 5 volts to over drive the 3 volt rated DC motor 208. Alternatively, the DC-DC step up converter 202 can provide a range of various voltage values to drive the DC motor 208 at different ratings in either the forward or the reverse directions.

In this embodiment, if the integral control electronics 210 failed and caused a direct short between the battery 206 and the DC motor 208 with the reversed biased Zener diode 204 (or a reversed biased Zener diode 204 in parallel with a Schottky diode 250), the DC motor 208 would not operate in the forward direction (i.e., there would be no drug delivery), and would have only a fraction of the rated torque in the rewind direction (or no rewinding if sufficient friction is present in the drive mechanism). For additional safety, alternative embodiments of the safety circuit 200 would include the DC-DC step up converter 202 such that it would only be enabled by an additional internal signal S2 (shown in dashed lines) from the control electronics 210. Thus, if the control electronics 210 were to fail, there would be no enable signal to provide the required step up voltage to drive the DC motor 208 in a "run away" condition. In preferred embodiments, the Zener diode 204 is contained within the DC motor package 212 (see also FIG. 7) so that the DC motor 208 is protected independently of the type of control electronics 210 to which the DC motor 208 is connected. In alternative embodiments, the Zener diode 204 could be contained within the control electronics and the electronics are then connected to a conventional DC motor (see also FIG. 8). In alternative embodiments, a second Zener diode may be used, which is reversed with respect to the first diode and in series with the first diode such that the DC motor operates similarly in both directions. In the event of direct short to the DC motor in the reverse direction, the battery voltage would not be enough to run the motor 208 in either direction. In further alternatives, the control electronics 210 may be separated from the DC-DC step up converter 202 and provided as a discrete element that is placed before or after the DC-DC step up converter 202.

In the first two embodiments, "run away" of the DC motor is substantially prevented However, if the system were to fail such that a short were maintained between the stepped up voltage from the DC-DC converter to the DC motor and/or the Zener diode failed, then the potential for motor "run away" exists with the above embodiments.

Figure 3:
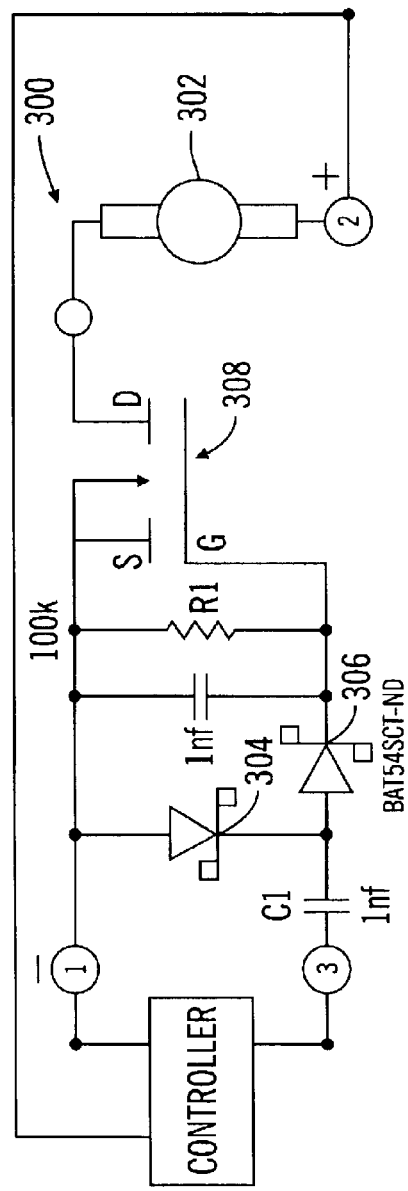
FIG. 3 is a schematic diagram of a safety circuit in accordance with a third embodiment of the present invention.
Figure 8:
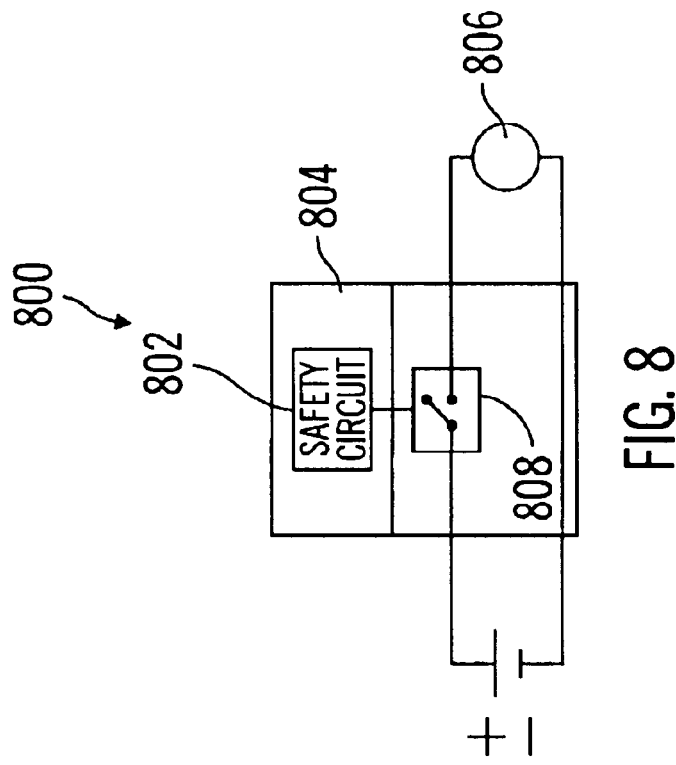
FIG. 8 is a simplified schematic of a motor and safety circuit in accordance with an alternative embodiment of the present invention.
Figure 7:
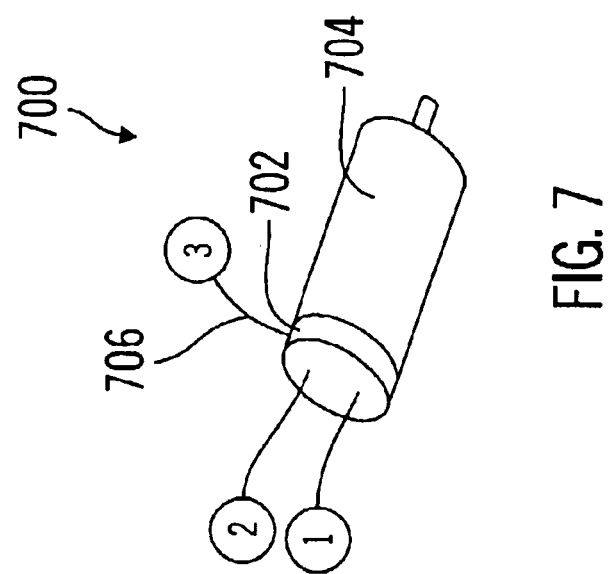
FIG. 7 is a perspective view of a motor in accordance with an embodiment of the present invention.

FIG. 3 illustrates a safety circuit 300 in accordance with a third embodiment of the present invention, which includes further enhancements to provide protection against DC motor 302 "run away". The safety circuit 300 includes additional electronics added to the DC motor package (as shown in FIG. 7) that are independent of the control electronics. Alternatively, the additional electronics may be included in the control electronics (as shown in FIG. 8) or as a separate set of control electronics (not shown). In preferred embodiments, the control electronics must provide a specific signal (at terminal 3) to the additional electronics to allow the DC motor 302 to operate. As shown in FIG. 3, the rated supply voltage from the battery (not shown) is supplied to terminals 1 and 2 as a negative and positive voltage potential, respectively, to control operation of the DC motor 302 in the forward direction. However, current will not pass through the DC motor 302 until a specific AC signal (e.g., a 3 volt Peak-to-Peak Square wave at approximately 32 kHz—see FIGS. 9–11) is provided to terminal 3 and the safety circuit 300 by the control electronics. This provides a second independent system to control the operation of the DC motor 302. For a "run away" to occur the control electronics must short the battery to the power terminals 1 and 2, and must also provide an AC signal to terminal 3 of the safety circuit 300.

Thus, if a direct short does occur between the battery and the power terminals 1 and 2 with the safety circuit 300, the DC motor 302 will not operate, since the required AC signal at terminal 3 is not present. Preferably, the safety circuit 300 uses two Schottky diodes 304 and 306 (e.g., BAT54SCT-ND from Zetex) and a FET 308 ((e.g., IRMLMS1902 from International Rectifier).

In operation, when the control electronics provide a positive DC voltage potential at terminal 2, and a negative voltage potential at terminal 1, the DC motor 302 will not operate since the gate G of the FET 308 does not have a positive signal applied to it derived from the input at terminal 3 of the safety circuit 300. In this situation, the gate G blocks the flow of current from the drain D to the source S of the FET 308. DC flow through terminal 3 is blocked by the capacitor C1. Thus, the DC motor 302 will not operate, if there is no AC signal applied to terminal 3 of the safety circuit 300.

Figure 9:
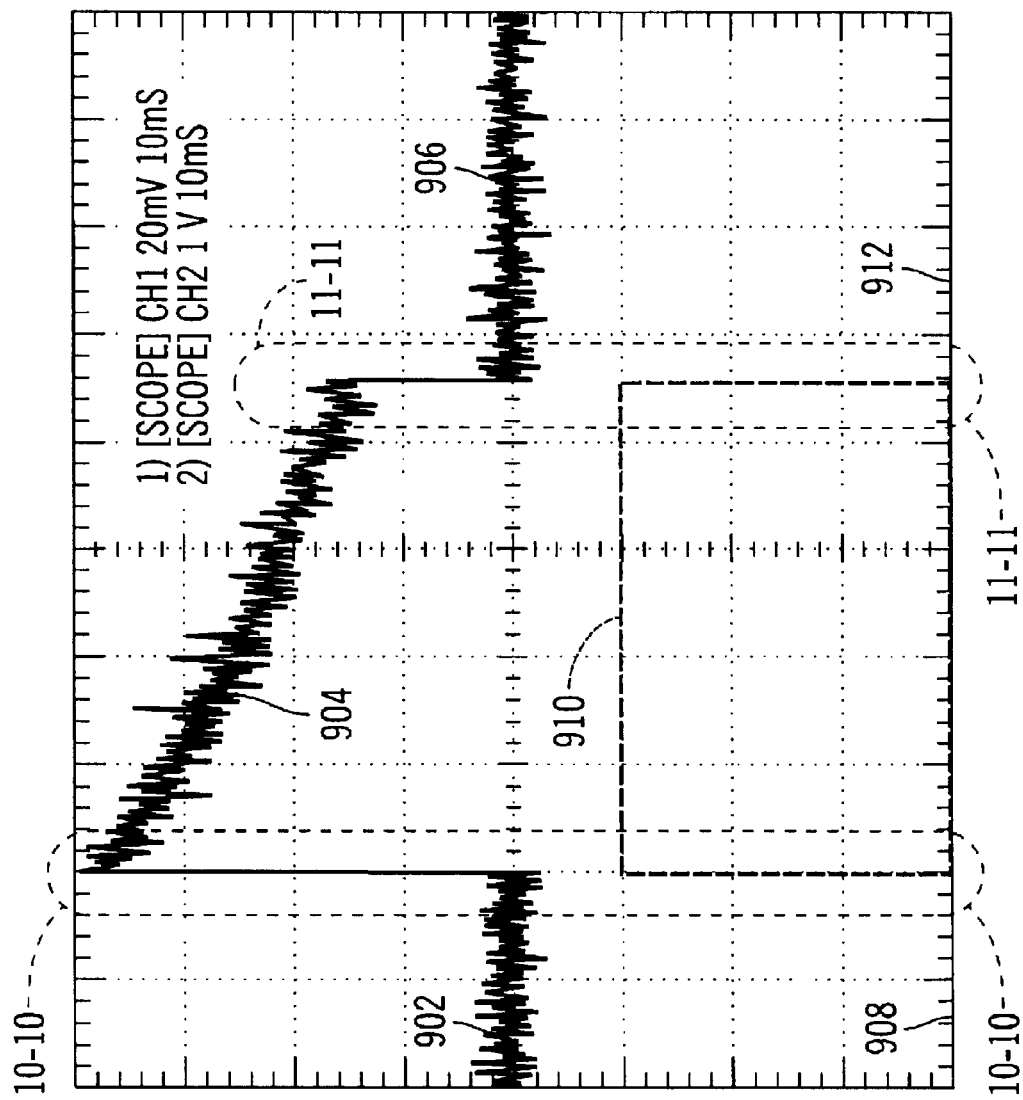
FIG. 9 is a waveform diagram illustrating operation of the safety circuit and power supplied to a DC motor in accordance with the embodiments of the present invention.
Figure 10:
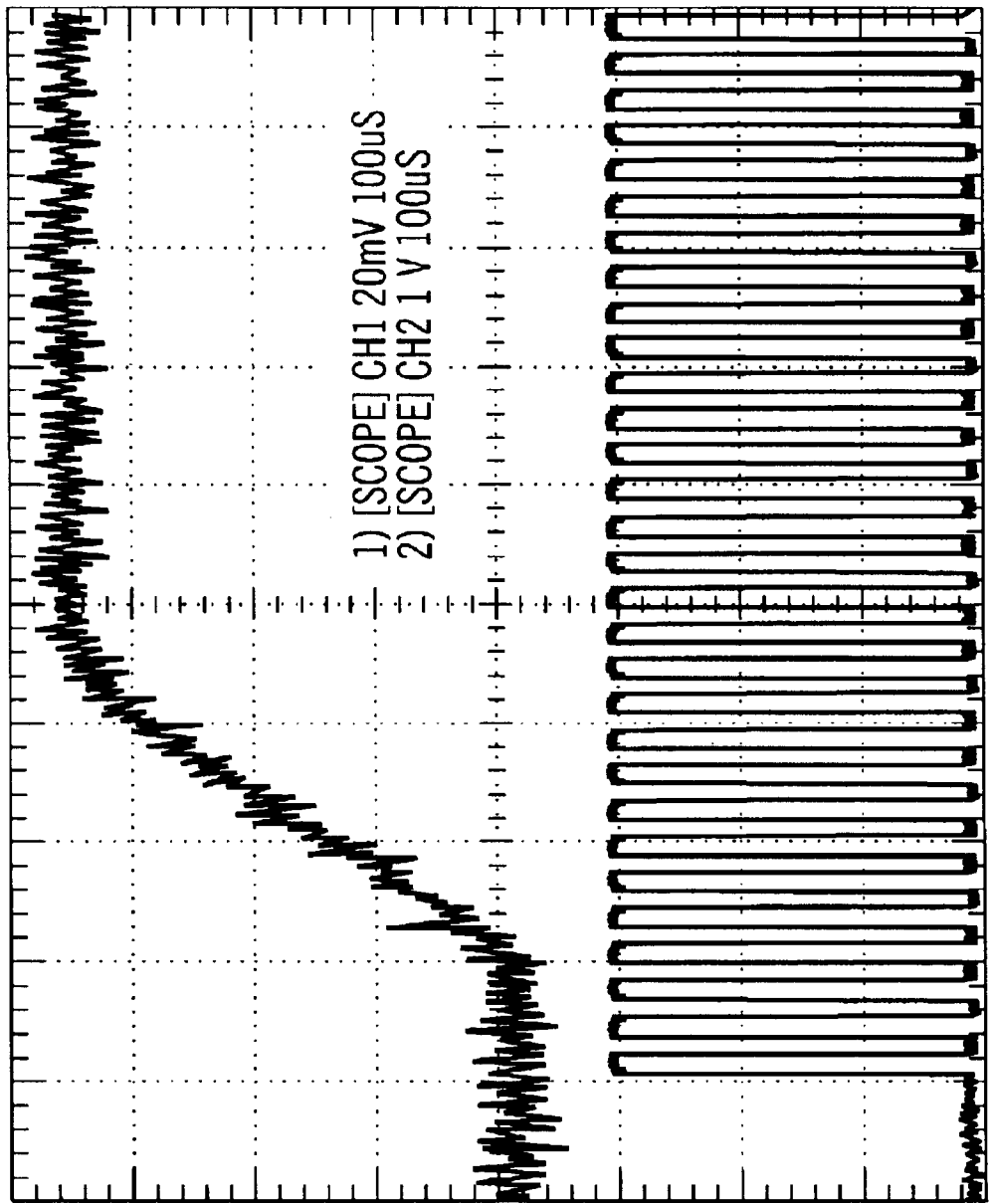
FIG. 10 is a waveform diagram illustrating operation of the safety circuit and power supplied to a DC motor that is an enlarged view of the portion shown in the dashed circle 10—10 of FIG. 9.
Figure 11:
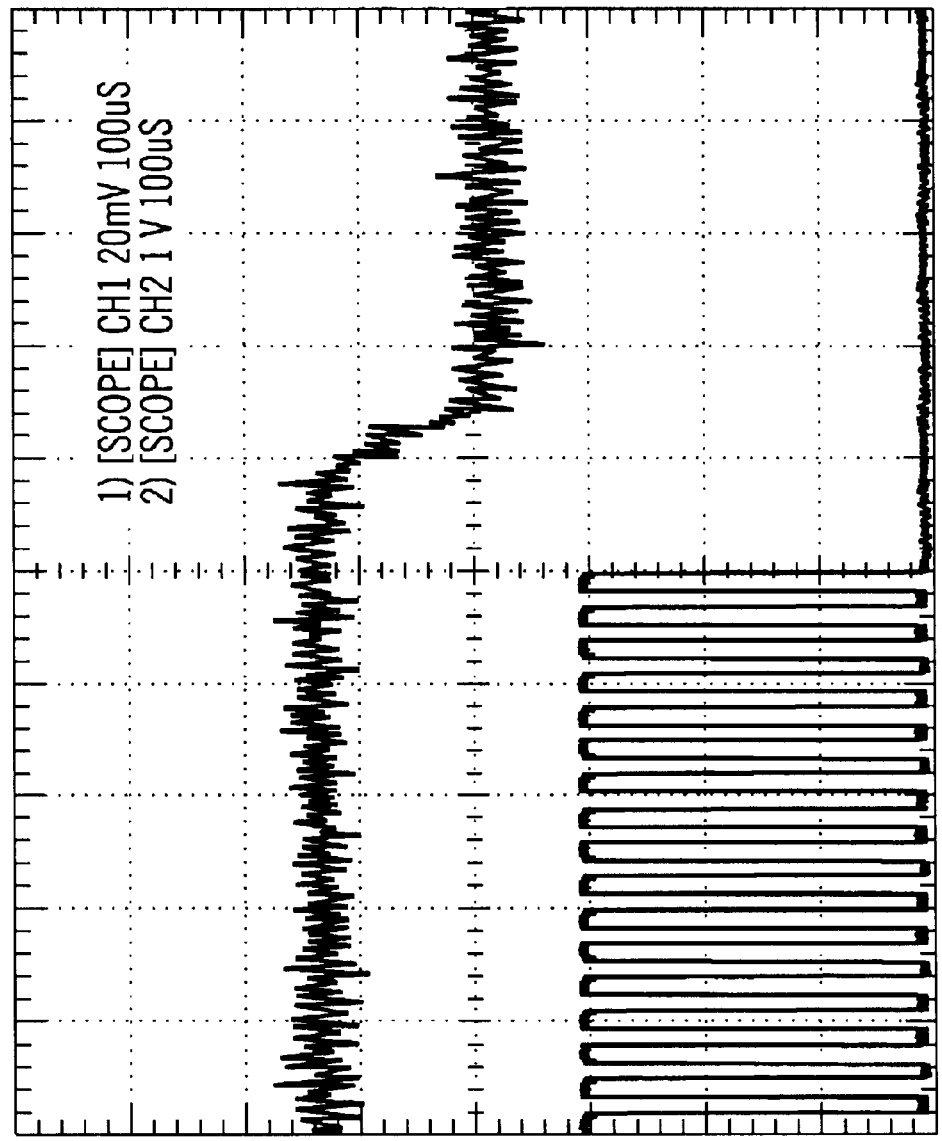
FIG. 11 is a waveform diagram illustrating operation of the safety circuit and power supplied to a DC motor that is an enlarged view of the portion shown in the dashed circle 11—11 of FIG. 9.

When an AC voltage potential signal (e.g., a 3 volt Peak to Peak square wave at a frequency of approximately 32 kHz—see FIGS. 9–11) is applied to terminal 3 of the safety circuit 300, Schottky diodes 304 and 306 rectify and double the signal to positively bias the gate G, current then flows from the drain D to the source S of the FET 308 and to terminal 1. This in turn drives the DC motor 302, which is connected to the positive DC voltage potential at terminal 2. In alternative embodiments, a different number of components, such as diodes, capacitors, resistors, or the like, may be used. In addition, the selection of the type of FET, diode, size of the voltage potentials on terminals 1, 2 and 3, the AC signal type (including duration of peaks, waveform and frequency), may be different, with the selection being dependent on motor nominal operating voltage, system friction, tolerances, safety issues, control electronics, or the like.

In preferred embodiments, the safety circuit 300 uses the additional AC signal to control the forward operation of the DC motor 302, since concerns over DC motor "run away" arise mainly from the possibility of over-delivery of a fluid due to the failure of the safety circuit 300. There is less concern for the situation, in which the fluid delivery system rewinds, since no fluid would be delivered in that scenario. However, in alternative embodiments, the drive system may also use an additional signal to control operation of the DC motor in the rewind direction.

Figure 4:
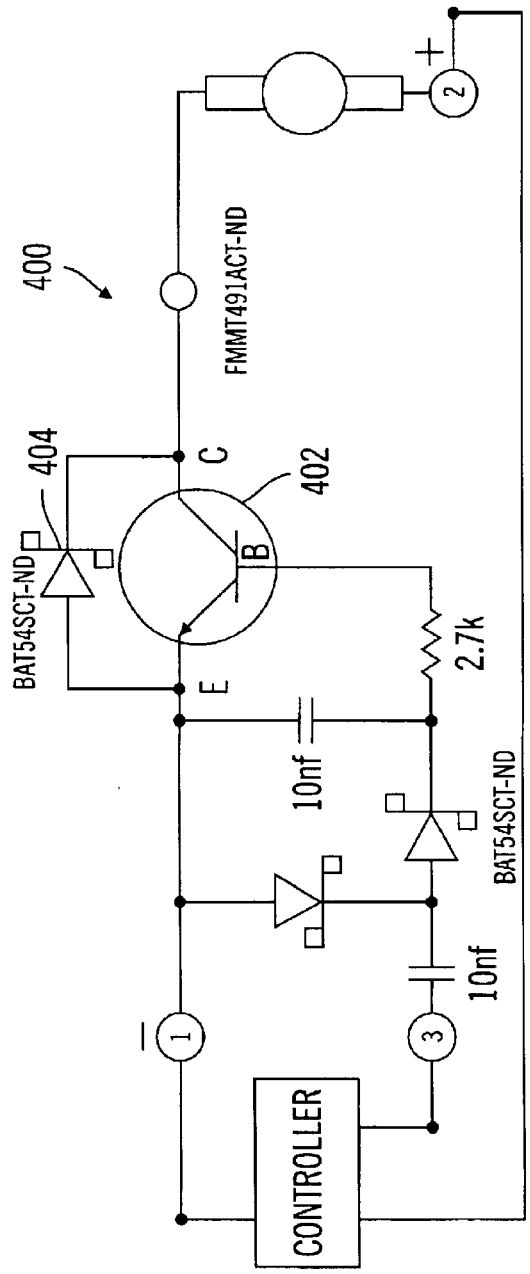
FIG. 4 is a schematic diagram of a safety circuit that is a variation of the embodiment shown in FIG. 3.

FIG. 4 illustrates a safety circuit 400 in accordance with a fourth embodiment of the present invention. This safety circuit 400 is similar to the embodiment of FIG. 3, but utilizes a BJT 402 (FMMT 491ACT-ND from Zetex) instead of the FET 308, and an additional Schottky diode 404 (e.g., BAT54CT-ND from Zetex).

FIGS. 5(a)–(c) illustrate a safety circuit 500 in accordance with a fifth embodiment of the present invention. This safety circuit 500 is also similar to the embodiment of FIG. 3, but utilizes FET 502 (IRLM1902 from International Rectifier) instead of the FET 308, and an additional Schottky diode 504 (e.g., BAT54CT-ND from Zetex).

Figure 6:
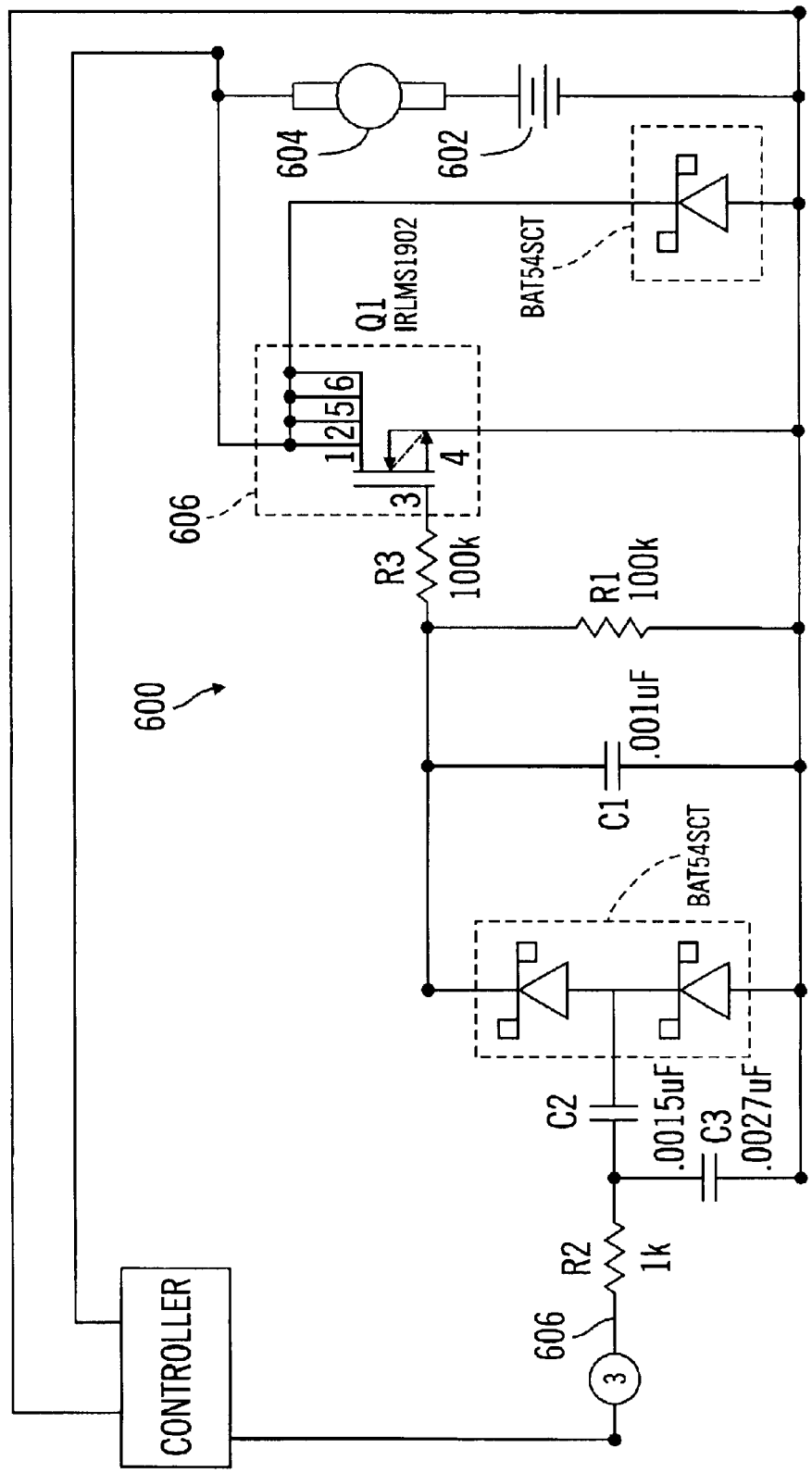
FIG. 6 is a schematic diagram of a safety circuit that is yet another variation of the embodiment shown in FIG. 3.

FIG. 6 illustrates a safety circuit 600 in accordance with a sixth embodiment of the present invention. This safety circuit 600 is similar to the embodiment of FIG. 3, but utilizes FET 606 (IRLM1902 from International Rectifier) instead of the FET 308, and an additional Schottky diode (e.g., BAT545CT-ND from Zetex). In addition, the capacitors and resistors are selected to form a bandpass filter to provide better noise isolation and circuit performance. Performance of the safety circuit 600 as it provides power to the DC motor 604 from a battery 602 is illustrated in FIGS. 9–11.

FIG. 7 illustrates a perspective view of a DC motor package 700 that includes a safety circuit 702 within the package 700 holding a DC motor 704. An advantage to this configuration arises from the fact that the DC motor 704 includes the safety circuit 702, which must be connected, and enabled, or the DC motor 704 will not operate. This minimizes the possibility that a DC motor 704 will be improperly installed in a fluid delivery device by assuring that an AC signal must be provided to the terminal input 3 on wire 706 to enable the DC motor 704 to operate. In alternative embodiments, as shown in FIG. 8, the fluid delivery system 800 includes an additional safety circuit 802 (i.e., in addition to other switches and controls found in the control circuitry), which is contained within the control electronics 804. The control electronics 804 are then connected to a standard, two-input DC motor 806, without the need for an additional connection to the DC motor 806. For instance, the safety circuit 802 operates a switch 808 to enable power to pass to and drive the DC motor 806.

FIGS. 9–11 illustrate operational waveforms for the safety circuit 600 (see FIG. 6) as DC current is applied to the circuit. As shown in FIG. 9, when DC current is applied to the DC motor 604 in graph section 902, no current is drawn since the AC enable signal in graph section 908 is not present. When the AC signal is applied in graph section 910, the DC current is quickly applied to the DC motor 604 by the battery 602, as shown by the graph section 904. When the AC enable signal is removed, as shown in graph section 912, the DC power supplied to the DC motor 604 is cutoff, as shown in graph section 906. FIGS. 10 and 11 highlight and expand portions of FIG. 9 to illustrate the AC signal used and the response of the safety circuit 600. The illustrated AC signal is at approximately 3 volts peak-to-peak at a frequency of approximately 32 kHz. However, in alternative embodiments, different shape waveforms, such as saw tooth, sinusoidal, or the like may be used. In addition, different voltage ranges may be used, with the selection being dependent on the rated motor output and the application in which the motor is being used. Further, higher or lower frequencies may be utilized, with the selection be dependent on the response characteristics of the safety circuit, noise, or the like. The delays observed in FIGS. 10 and 11 are a result of the smoothing and bandpass filters used in the safety circuit 600. For instance it takes approximately 125 microseconds for the DC motor 604 to respond after the AC signal is provided, and about 80 microseconds for the DC motor 604 to respond to termination of the AC signal. One advantage of having the DC current ramp up and down is that it minimizes the effects of voltage spikes and electromagnetic interference.

Further embodiments may employ alternative or additional safeguards comprising or including selective potting of circuit portions and/or elements. As is well known, potting material protects electrical and electronic components from external effects, such as moisture and other contaminants. However, even when generally well-sealed against penetration by moisture and other contaminants, known potting materials typically fail to protect the electrical system against long-term contaminant penetration due to creep, differences in thermal expansion (heat cycling), poor sealing or adhesion; poor workmanship; degradation of the potting materials mechanical working, such as flexing, bending, torquing, shear, shock, vibration, tension or compression; or the like. For example, moisture diffusion through the potting material will likely detrimentally affect the performance of the electrical system and may lead to unpredictable system failures.

As an example, infusion devices like those described above may employ a drive system including a power driver portion and a controller portion. The controller portion provides a signal to the power driver portion to control the power driver portion. The power driver portion transfers power from a power source to the drive system, such as a DC motor, a powered and/or controlled drive mechanism, or the like, that drives the infusion device. Typical power sources include, but are not limited to, a battery, power supply, AC source, DC source, solar cell, or the like. In one possible failure mode, the moisture may penetrate the potting material covering the power driver portion and cause a direct short from the power source to the drive system. Thus, it would be possible for the drive mechanism to run away. As a result, all of the medication contained in the infusion device may be infused over too short a period resulting in injury or death to the patient. However, in another possible failure mode, the contaminant may first penetrate the potting material covering the controller portion of the drive system and/or the power source. If an electrical fault, a short-circuit for example, occurred in the controller portion as a result, the likelihood of drive system runaway may be reduced. This is because the controller portion and/or power source of the drive system may become disabled before the contaminant penetrates and short-circuits the power driver portion of the drive system, which would prevent power from reaching the DC motor even if the power driver portion provides a current path due to short-circuits. Thus, by selectively potting critical circuit portions or elements, an electrical fault may be selectively isolated to a predetermined portion, element, or circuit path within an electrical or electronic system, or at least the electrical fault will occur in the un-potted non-critical portion, element, or circuit before an electrical fault develops in a potted critical portion, element, or circuit. In this manner, a failure of that system may be controlled to occur in a non-critical portion of the system. In other words, a non-critical portion of the system may be left exposed to any contaminants such that the system fails in a defined or safe manner, such as turning the infusion device (and/or drive system) off, indicating that a failure and/or leak has occurred, placing the device in a stable unalterable operational state, or the like.

Figure 12:
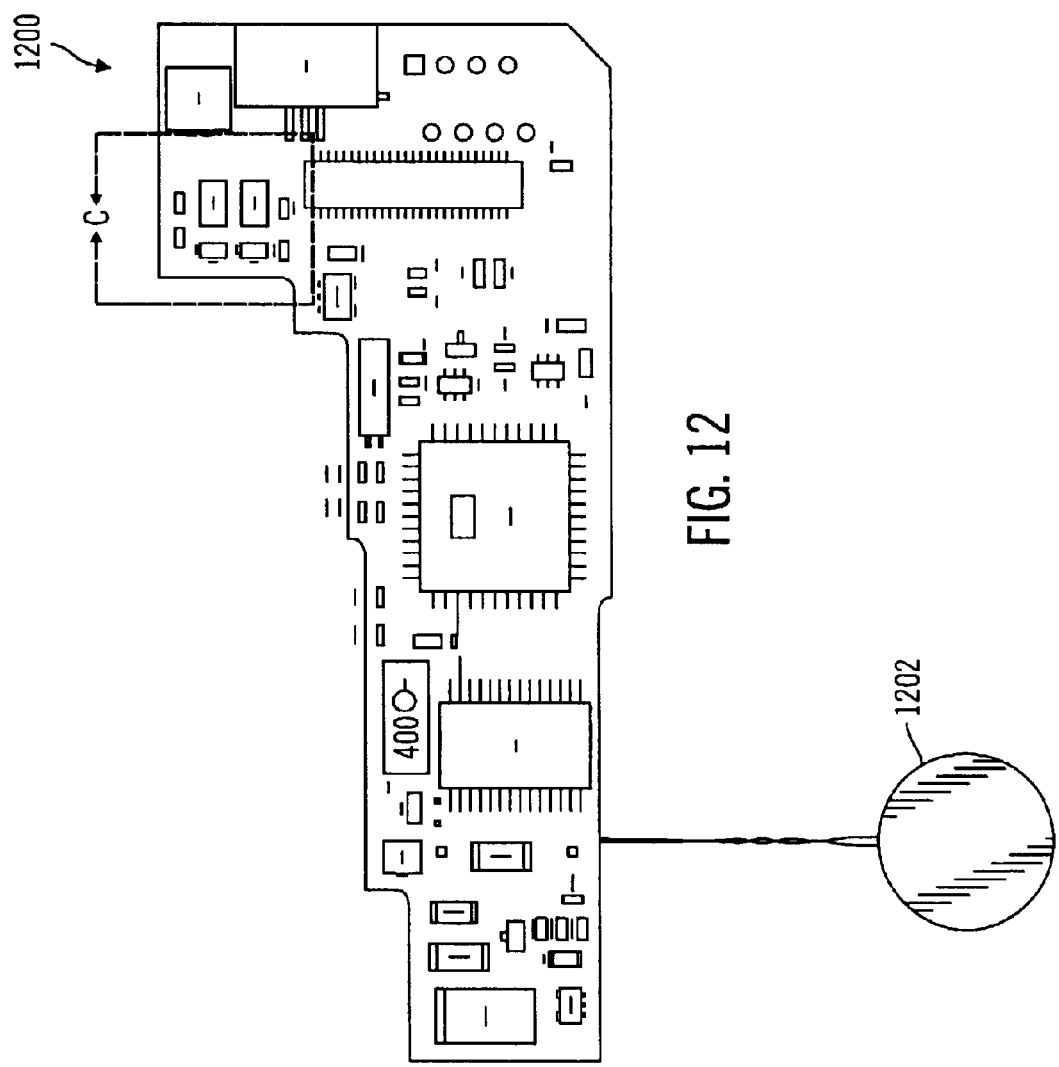
FIG. 12 illustrates a schematic diagram of a printed circuit board used in a drive system for a DC motor in accordance with an embodiment of the present invention.

FIG. 12 illustrates a schematic diagram of an embodiment of a printed circuit board 1200 used in a drive system for a DC motor 1202. DC motor 1202 may be used, for example, in a medical infusion device. The portion of circuit board 1200 enclosed in the dashed lines and designated as view C comprises a portion of the drive system used as a power driver circuit for transferring power from a power source (not shown) to the DC motor 1202. The remainder of circuit board 1200 comprises a controller portion of the drive system used for enabling and disabling the power driver circuit. The controller portion may include control electronics and/or one or more microprocessors. The controller portion may further include a step up converter as described above with respect to FIGS. 1 and 2. Furthermore, the controller portion may also include a safety circuit such as that described with reference to FIG. 6. Alternatively, the safety circuit may be integral to the DC motor.

Figure 13:
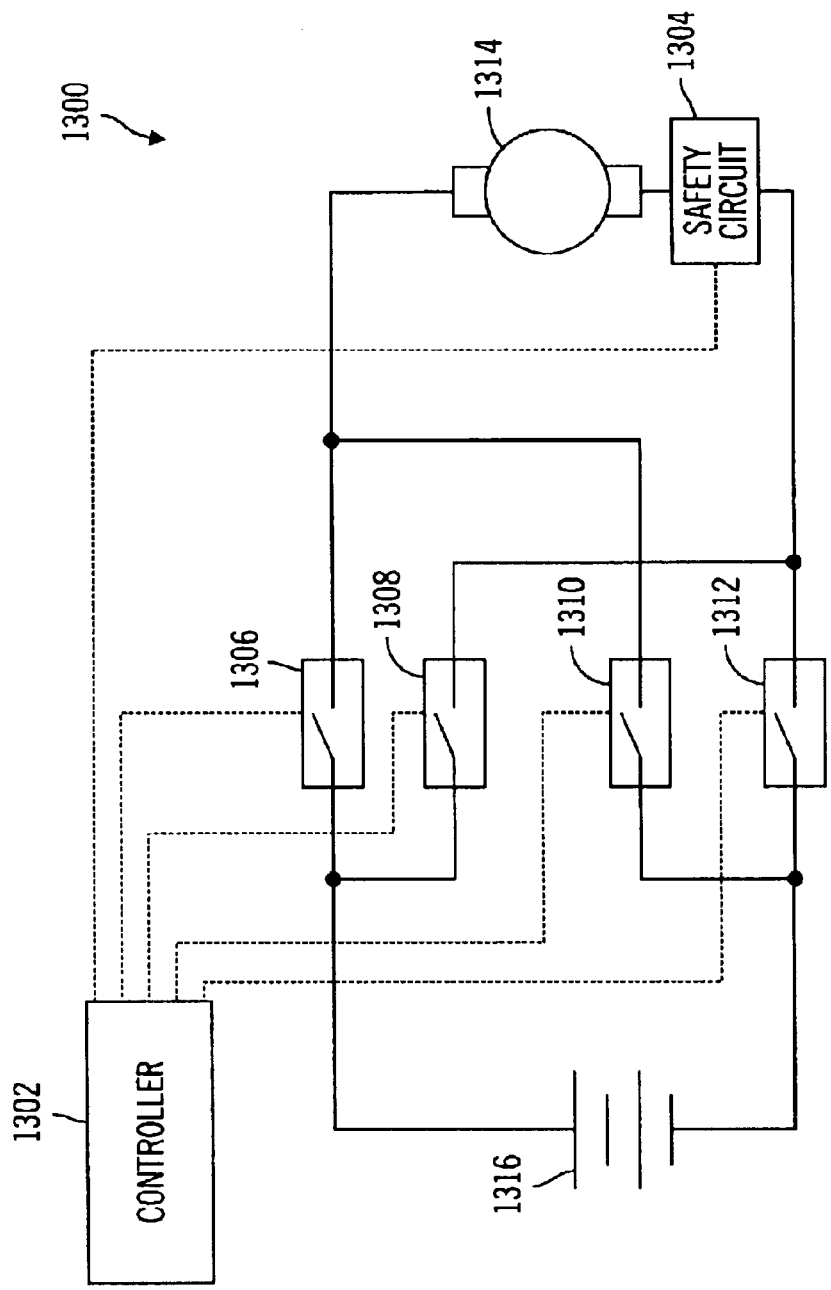
FIG. 13 illustrates a simplified schematic diagram of an embodiment of a power driver circuit used in a drive system for a DC motor in accordance with an embodiment of the present invention.

FIG. 13 shows a simplified schematic diagram of an embodiment of a power driver circuit 1300 shown as view C in FIG. 12. FIG. 13 further shows simplified block diagrams of the controller 1302 and safety circuit 1304, illustrating in a simplified manner how they are coupled to the power driver circuit 1300 in one embodiment. In FIG. 13, the controller 1302 is not co-located with the power driver circuit 1300 on circuit board 1200. In further embodiments, safety circuit 1304 may be co-located with the controller 1302 on the controller portion of circuit board 1200 or may, in other embodiments, be integral to DC motor 1314. Alternative embodiments may be utilized with more or less complicated circuits.

The power driver circuit 1300 shown in FIG. 13 has an H-bridge configuration including first and second pairs of switching elements having conducting and non-conducting states. The first and second pairs of switching elements, as well as the safety circuit 1304 are coupled to the controller as represented by the dashed lines. The first pair of switching elements 1306, 1312 are enabled to be in a conducting state to conduct a first current from a first terminal of battery 1316, through the winding of the DC motor 1314 and back to a second terminal of battery 1316, when a first signal is received from the controller 1302. If the controller 1302 also sends an enable signal to the safety circuit, a first current will be established in the winding of the DC motor 1314 and the motor may turn in a first direction.

The second pair of switching elements 1308, 1310 are enabled to be in a conducting state to conduct a second current from the first terminal of battery 1316 through the winding of the DC motor 1314 and back to the second terminal of battery 1316 through the winding of the DC motor 1314 when a second signal is received from the controller 1302. If the controller 1302 also sends an enable signal to the safety circuit, a second current will be established in the winding of the DC motor 1314 and the motor may turn in a second direction. Thus, bi-directional current flow is established in the stator winding since the first current is in a direction through the winding that is opposite from the direction of the second current.

It can be seen from FIG. 13 that if a contamination induced short circuit occurs in the power driver circuit 1300 where either the first or second pair of switching elements are short circuited, it would be possible for the DC motor 1314 to run away. It can also be seen from FIG. 13 that the first and second pairs of switching elements are enabled and disabled by the controller 1302. Thus, according to one embodiment of the present invention, the controller 1302 is un-potted and is thus more likely to be exposed to a contaminant and become disabled prior to the contaminant shorting the first or second pairs of H-bridge switching elements. Once the controller 1302 is disabled, the controller fails to provide enable signals to the first or second pair of switching elements and/or to the safety circuit 1304. Therefore, the drive system may be disabled before the first and/or second pairs of switching elements can be short circuited, thus protecting against DC motor run away.

Figure 14:
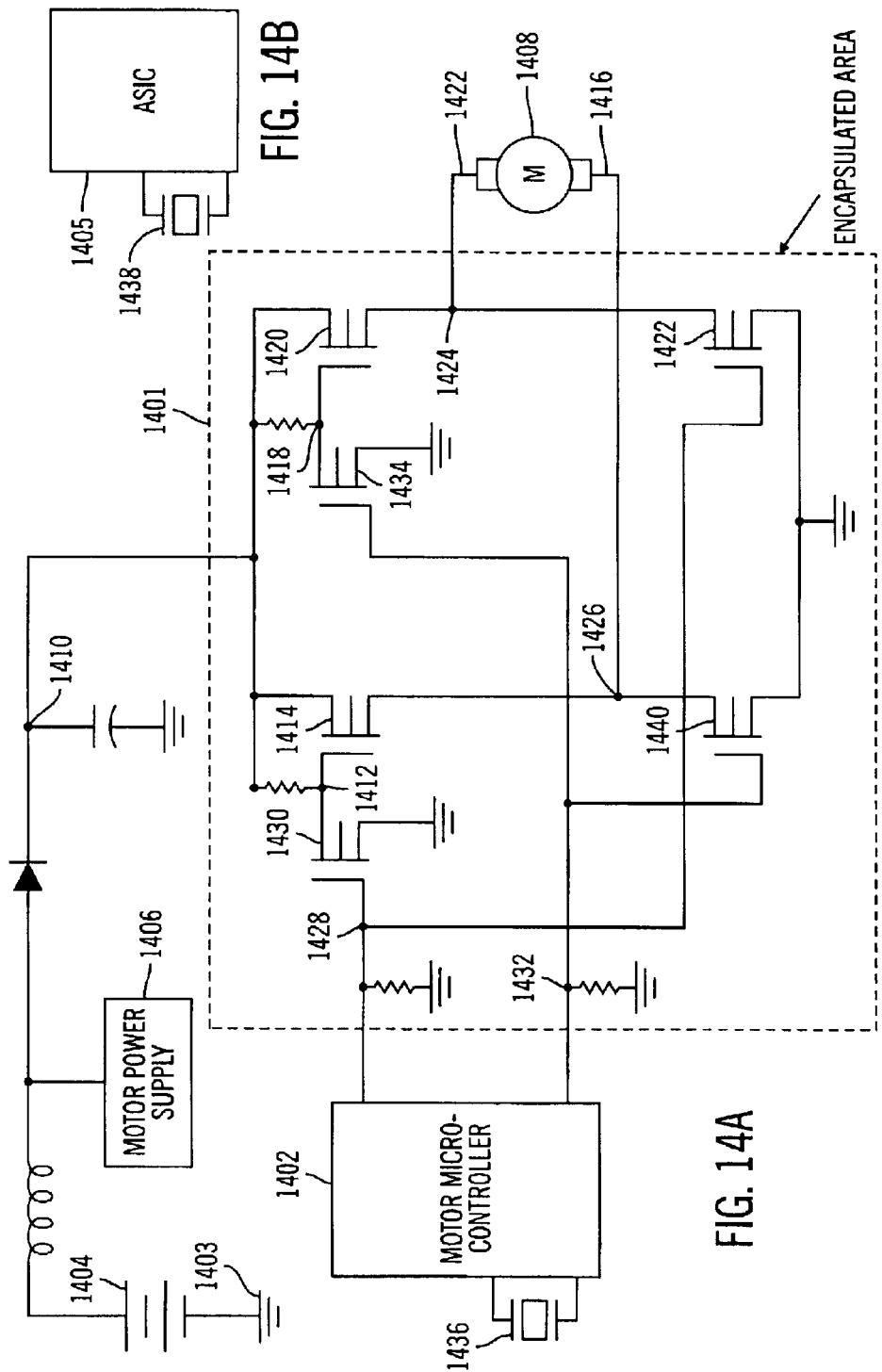
FIG. 14A illustrates a schematic circuit diagram of a drive system for a DC motor in accordance with an embodiment of the present invention.
FIG. 14B illustrates an ASIC chip for implementing a safety circuit in accordance with an embodiment of the present invention.

Possible effects of a contamination induced short circuit on the power driver circuit of FIG. 13 are described in more detail with reference to FIG. 14A. FIG. 14A illustrates a schematic diagram of a component level view of one embodiment of a drive system as shown in FIG. 13, including a DC motor 1408, an H-bridge configuration of switching elements 1414, 1420, 1440, and 1442, a controller 1402, and a power source 1404, 1406. For the sake of clarity, it will be assumed when describing the operation of the power driver circuit shown in FIG. 14A that the DC motor 1408 is a normal DC motor and not a safety motor. Therefore, a safety circuit, such as the safety circuit 1304 shown in FIG. 13, is not shown in the circuit in FIG. 14A. It should be understood, however, that if a safety motor were used in place of a normal DC motor, forward motion of the DC motor 1408 in the following description of FIG. 14A would not occur unless the conditions of the safety circuit were met as described above with regard to various embodiments of the safety circuit. An exemplary embodiment of a safety circuit 1405 may be implemented in an ASIC chip 1405 having a crystal oscillator 1438, as shown in FIG. 14B.

Referring again to FIG. 14A, the portion of the drive system enclosed within dashed line 1401 represents one embodiment of the H-bridge configuration of switching elements and associated components corresponding to the generalized illustration of the power driver circuit shown in FIG. 13. The controller (corresponding to controller 1302 of FIG. 13) includes a motor micro-controller 1402 having a crystal oscillator 1436. The power source comprises a battery 1404 and motor power supply 1406 coupled to the power driver circuit to provide power to DC motor 1408. In one embodiment, the power supply output 1410 of motor power supply 1406 is set to 2 volts for forward mode and is set to 5 volts for reverse mode. Due to the configuration of the power supply, the battery 1404 voltage is present at the power supply output 1410 when motor power supply 1406 is disabled. Thus, unless the battery is removed or shorted, a minimum voltage of about 1.5 volts is present at power supply output 1410.

Various possible short circuit conditions may occur in a drive system and may lead to DC motor run away. For example, a contamination induced short circuit condition may occur which shorts point 1412 to ground 1403. As a result of this condition, switching element 1414 will be turned on and a first terminal 1416 of DC motor 1408 will be energized with the voltage present at power supply output 1410. Similarly, if point 1418 is shorted to ground 1403, switching element 1420 will be turned on and the other terminal 1422 of DC motor 1408 will be energized with the voltage present at power supply output 1410. Thus, either of these short circuit conditions allows power to be supplied to one side of the DC motor 1408. If a short circuit also occurs that shorts either point 1424 or 1426, respectively, to ground 1403, a current path is created which will result in the running of DC motor 1408.

A further contamination induced short circuit condition may occur that causes a short across the source and drain terminals of switching element 1414. If this condition occurs, switching element 1414 will be bypassed and terminal 1416 of DC motor 1408 will be energized with the voltage present at power supply output 1410. Similarly, a short circuit condition may occur that causes a short across the source and drain terminals of switching element 1420. If this condition occurs, switching element 1420 will be bypassed and terminal 1422 of DC motor 1408 will be energized with the voltage present at power supply output 1410. If a short circuit also occurs that shorts either point 1424 or 1426 to ground 1403, a current path is created that will result in the running of DC motor 1408.

Another contamination induced short circuit condition may occur that causes a short across the source and drain terminals of switching element 1430. If this condition occurs, switching element 1430 will be bypassed and one entire arm of the H-bridge will be turned on and the DC motor will move in the forward direction. Similarly, a short circuit condition may occur that causes a short across the source and drain terminals of switching element 1434. If this condition occurs, switching element 1434 will be bypassed, and one entire arm of the H-bridge will be turned on and the DC motor will move in the reverse direction.

Possible short circuit conditions that may occur in the drive system and may lead to disabling the drive system before DC motor run away can occur will now be described. A contamination induced short circuit condition may occur that shorts point 1428 to ground 1403. If this condition occurs, switching element 1430 cannot turn on and the drive circuit will be disabled in the forward direction. Similarly, a short circuit condition may occur that shorts point 1432 to ground 1403. If this condition occurs, switching element 1434 cannot turn on and the drive circuit will be disabled in the reverse direction.

An additional contamination induced short circuit condition may occur that shorts the crystal oscillator 1436 of the motor micro-controller 1402. If this condition occurs, motor microcontroller 1402 may not operate to activate motor control signals. Another contamination induced short circuit condition may occur that shorts battery 1404. If this condition occurs, there will be no power to the motor power supply 1406 and the drive system will be disabled.

A further contamination induced short circuit condition may occur that shorts power supply output 1410 to ground 1403. If this condition occurs, power cannot be supplied to the motor and the drive system will be disabled.

Yet another contamination induced short circuit condition may occur in a safety motor embodiment that shorts crystal oscillator 1438 of the safety circuit 1405. In a safety motor embodiment, if this condition occurs, the ASIC cannot generate the safety circuit signal that will allow the safety motor to move, as described above.

As seen from the above description of FIG. 14A, particular short circuit conditions are safer than others, for instance, several of the short circuit conditions described above may disable the DC motor from running, while several others may result in DC motor run away. By selectively encapsulating the portions of the drive system where a short circuit condition or other electrical fault may result in motor run away (i.e., the portion enclosed by dashed line 1401), embodiments of the present invention protect those portions from exposure to contaminants that may cause motor run away, and allow for a controlled, predictable or desired failure of the device.

Furthermore, embodiments of the invention leave un-encapsulated the portions of the drive system, where a short circuit condition or other electrical fault is more likely to result in the drive system becoming safely, controllably, desirably or predictably disabled or failed. Thus these un-encapsulated portions increase the likelihood that a contaminant induced electrical fault occurs first in the un-encapsulated portion, to disable the drive system before the contaminant can penetrate and short circuit the encapsulated portion. Therefore, embodiments of the present invention provide for a controlled failure of an electrical system, such as the drive system, or other device as described above.

Referring again to FIG. 12, in one embodiment a potting material is used to selectively encapsulate the power driver circuit portion of the circuit board 1200 shown in view C and schematically in FIGS. 13 and 14A and 14B. In some embodiments, a safety circuit may be integral to the DC motor. In this embodiment the safety circuit may be encapsulated by the potting material to protect it from contaminants. In one embodiment, the potting material may be any moisture-resistant potting material such as, but not limited to parylene, room temperature vulcanizing silicone elastomers (RTV's), silicone, epoxies, adhesives, plastics, or the like.

In some embodiments, the remainder of circuit board 1200, which includes the controller portion, remains un-encapsulated. Thus, when circuit board 1200 is incorporated into the drive system, the controller portion of circuit board 1200, which is un-encapsulated and exposed, may be one of the first portions of the circuit board 1200 that comes in contact with any contaminant. After being exposed to a contaminant, the drive system may become disabled, as a result of an electrical fault induced by the contaminant in the controller portion, which would prevent the controller portion from controlling the encapsulated power driver circuit before the power driver circuit is exposed to the contaminant. Therefore, a contaminant induced electrical fault, such as a short circuit condition, may be controllably isolated to a selected portion of an electrical system.

Yet, further embodiments may employ, alternatively or in addition to selective potting, one or more dissolvable circuit elements, such as fuses, located in a current path of electrical systems. For example, a dissolvable circuit element may include a fuse or circuit formed from metallic powder or unidirectional carbon fibers held in a dissolvable matrix, such as starch, sugar, or the like, combinations of contaminant sensitive materials, or the like, located in series with the circuit path from the output 1410 of the motor power supply 1406 to the power driver circuit enclosed within dashed line 1401. (See FIG. 14). Thus, if the dissolvable circuit element comes into contact with a contaminant, it dissolves and opens the circuit path and no power is available to run DC motor 1408. Other embodiments may employ any suitable locations or current paths for the one or more dissolvable circuit elements.

As shown in the simplified schematic of FIG. 15, in other embodiments, the dissolvable fuse 1502 or circuit is part of the power supply portion 1504 of circuit 1500. A switch, relay, or the like 1510 is be used to provide power from the power supply 1514 to the power driver circuit 1506 (such as an H-bridge, or the like) along a power line 1516. The dissolvable fuse 1502 or circuit is used to provide a signal to the relay 1510 along a signal line 1508 to keep the relay 1510 closed, and thus, power supplied along the power line 1516. If the dissolvable fuse 1502 or circuit dissolves, then the signal on the signal line 1508 is removed, the relay 1510 opens, and no power is provided along the power line 1516 to the power driver circuit 1506. Consequently, the power driver circuit 1506 cannot supply power to the load 1512 (such as a motor, actuator, pump, or the like) even if a controller 1518 commands that the load 1512 be turned-on or if the potted power diver circuit 1506 later fails and incorrectly tries to provide power to the load 1512. In this embodiment, the dissolvable fuse 1502 or circuit can be thin and easily dissolvable, because it carries very little current to keep the power-carrying relay 1510 closed.

As shown in the partial schematics of FIGS. 16 and 17, in embodiments that use a dissolvable fuse 1602, 1702 or circuit in a power line 1604, 1704 that actually carry the power, the dissolvable fuse 1602, 1702 or circuit must be carefully designed to dissolve quickly, yet be thick enough to carry the current load from a power source 1608, 1708 through a power driver circuit 1606, 1706 to a DC motor 1610, 1710, or the like. In further alternatives, the dissolvable fuse 1602 or circuit may control one or more individual switches or relays (not shown) that control each of the power pathways in a power driver circuit.

Figure 18:
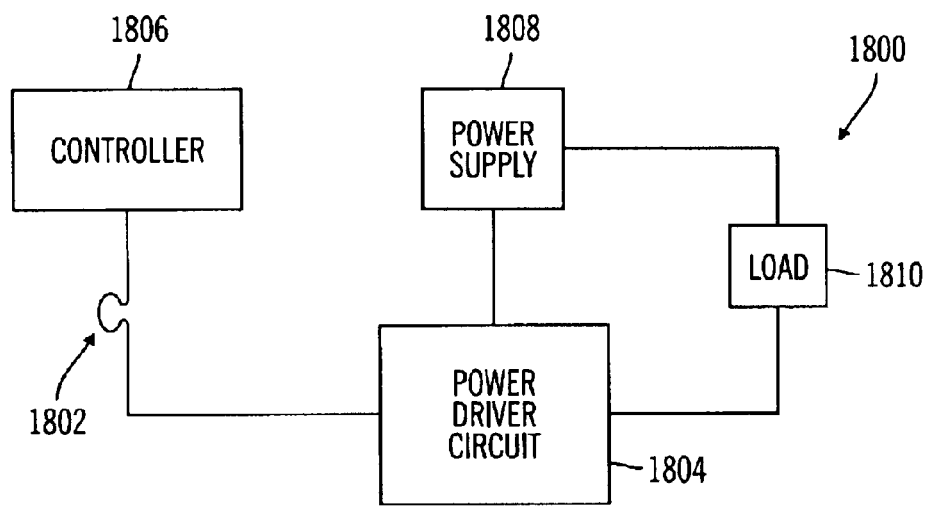
FIG. 18 illustrates a simplified schematic circuit diagram of a dissolvable fuse, switch, or circuit used to carry a controller signal in accordance with an embodiment of the present invention.

In further alternative embodiments, as shown in FIG. 18, a dissolvable fuse 1802 may be un-potted while critical portions (such as the power driver circuit 1804) of the remaining circuit 1800 are potted for protection. If a contaminant contacts the circuit 1800, the dissolvable fuse 1802 would dissolve preventing a signal from a controller 1806 from reaching the power driver circuit 1804. Without a signal from the controller 1806, the power driver circuit 1804 will not connect power from a power supply 1808 to a load 1810. And the circuit 1800 is disabled in a safe manner. The dissolvable fuse 1802 may be designed to carry very little electrical load and therefore dissolve very quickly since the signal from the controller is likely to be at a relatively low power compared to portions of the circuit 1800 that carry power from the power supply 1808.

Figure 19:
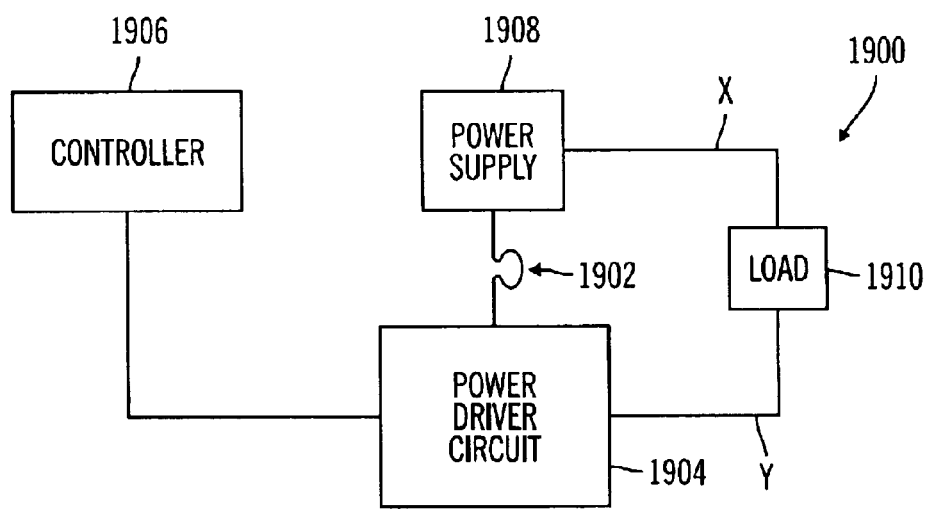
FIG. 19 illustrates a simplified schematic circuit diagram of a dissolvable fuse, switch, or circuit used in a power-carrying portion of a circuit, in accordance with an embodiment of the present invention.

In still further alternative embodiments, as shown in FIG. 19, a dissolvable fuse 1902 may be un-potted while critical portions (such as the power driver circuit 1904) of the remaining circuit 1900 are potted for protection. If a contaminant contacts the circuit 1900, the dissolvable fuse 1902 would dissolve preventing power from a power supply 1908 from reaching the power driver circuit 1904. Even if a controller 1906 continues to send signals the power driver circuit 1904 to provide power to a load 1910, no power will be available. And even if the power driver circuit were to fail and inadvertently try to connect the power supply 1908 to the load 1910, still no power would be available to the load 1910.

In still other embodiments, the dissolvable fuse 1902 may be located along line 'X' between the power driver circuit 1904 and the load 1910, or along line 'Y' between the load 1910 and the power supply 1908. In fact, one or more dissolvable fuses may be used between the power supply 1908, the power driver circuit 1904, and the load 1910. If any of the dissolvable fuses is touched by a contaminant, the portion of the circuit 1900 that carries power will have at least one open and thus be disabled.

It should be understood that in all embodiments that employ a dissolvable fuse, that the dissolvable fuse might be a fuse, switch, or circuit.

In alternative embodiments, the dissolvable fuse or circuit may open a circuit under normal conditions, and close the circuit upon detection of contamination.

The dissolvable circuit elements may be dissolved by contact with a particular contaminant, such as moisture, fluids, oil, particular gases, or the like. In one embodiment, a selected portion or portions of the electrical system are potted, and the dissolvable circuit elements are left un-encapsulated by potting material. In this manner, the dissolvable circuit elements may be exposed to the contaminant and thus dissolve and cause an open in the current path which may disable the electrical system before a contaminant induced electrical fault may occur in the selected potted areas. In another embodiment, only the contaminant dissolvable circuit elements may remain un-encapsulated by the potting material. The remainder of the electrical system may be encapsulated.

In further alternatives, the dissolvable fuse or circuit may dissolve upon exposure to excess temperature, light, current, voltage, or the like. Thus, contaminants may be solid, gas or liquid, or an unacceptable change in electrical state, or physical state.

Still other embodiments may employ, alternatively or in addition to selective potting and/or contaminant dissolvable circuit elements, one or more contaminant sensing elements, such as humidity sensors, gas sensors, fluid sensors, pressure sensors, temperature sensors, accelerometer, light sensors, or the like. In one embodiment, the contaminant sensing elements may be left un-encapsulated by potting material such that a contaminant may be sensed by the contaminant sensing elements before the contaminant may contact other portions of the electrical system. In one embodiment, the one or more contaminant sensing elements may comprise one or more pairs of conductive plates or other conductive members separated by a small distance and may be situated in a manner such that a contaminant may be received between the plates. Thus, the contaminant may short a pair of plates together. The shorting together of the plates may, in one embodiment, complete a circuit. The completed circuit may then convey, for example, a signal to a controller or other device operative to shut down the system in a defined or safe manner. Other embodiments may employ any other suitable contaminant sensing elements.

In further embodiments, the dissolvable fuse 1502, 1602, 1702, 1802, and 1902 in FIGS. 15–19, respectively, is replaced with a contaminant sensing element that is activated upon sensing the presence of a contaminant, electrical change or physical change. Thus, the contaminant-sensing element may open a switch upon sensing the presence of a contaminant, electrical change, or physical change to disable the system. In alternative embodiments, the contaminant-sensing element may open a circuit under normal conditions, and close the circuit upon sensing the presence of a contaminant, electrical change, or physical change to disable the system.

In all of the above embodiments, when a disabling event occurs, the controller may be operative to produce some form of user-perceptible signal in response to the completed circuit to alert a user that a contaminant has been sensed within the system. For example, an warning message may be displayed on a display associated with the electrical system. As another example, an audio tone may be generated on a speaker or other output device associated with the electrical system to alert a user that the electrical system has detected a fault and is presently shutting down. As yet another example, the electrical system may vibrate in a manner that a user may detect. In some embodiments, the device may be further operative to safely shut down the electrical system once a contaminant has been sensed. In further embodiments, the controller or other device may require a reset before the electrical system may again become operational. In still other embodiments, the system may send a signal to another device, shut down permanently, operate a predetermined steady state or rate, trigger an irreversible destruction or disablement of the device, or the like.

In the embodiments described above, the selective potting has been described in relation to the power driver circuit, a controller, and a DC motor or drive system. However, the embodiments of the present invention are not limited to the specific illustrations, and many variations in layout, type of devices and components may be made. For instance, the selective potting may be directed to causing the power supply portion to be the portion to fail controllably by leaving it as the portion that is left un-encapsulated and it then fails when contaminants are present. In other embodiments, the motor or drive system contains the controller, and the motor is left un-encapsulated to controllably fail when exposed to a contaminant.

Although primarily illustrated for infusion devices, the embodiments of the present invention described above are applicable to the many other devices and systems described above. In other words, one or more of the circuit portions described above (e.g., but not limited to, the controller portion, the power driver circuit portion, the power source, the DC motor, or the like), may be substituted by a different component or system to selectively control the failure of that component or system. For example by way of illustration, but not limited to, the selective potting could be applied to sensor monitors and systems. The selective potting may be applied to expose and disable the signals coming from a sensor. For instance, in one type of glucose sensor, the signal is measured as a change in current based upon the interaction of the glucose molecule with a reagent, oxidase, reactive agent, or the like, to produce an electrical signal. If the sensor monitor is exposed to a contaminant, the signal would be disrupted or shorted to prevent erroneous signals from reaching the monitor. The sensor may also display an error message, or provide an indication of failure or system compromise. In still other embodiments, the sensor may be controlled to produce a steady state signal of the last reading along with the indication of failure or compromise. In other embodiments, the power to the sensor may be interrupted. Sensors may be used to monitor other biological functions or processes, as described above, and should not be viewed as being limited to glucose sensors. The sensor applications apply to meters as well as monitors, and covers applications that take discrete measurements, continuous measurements, near-continuous measurements, pulsatile measurements, intermittent Controlled failure can be important in sensor monitoring applications, since the sensors are often used to determine the quality or compliance in a process, therapy, or the like. In medical applications, the user may be dependent on sensor readings to determine the amount of medication to administer. Erroneous data could make treatment ineffective or deadly. If the sensor is part of an automated or semi-automated closed loop system that includes a sensor system, a patient could be adversely affected during a sensor system failure without notice, since the aim of a closed loop system is to minimize user interaction with the system. A user could then get too much or too little medication, drugs, and/or fluids.

From the above, one of ordinary skill in the art can readily appreciate the applicability of embodiments of the present invention to other devices and systems that require and/or benefit from the controlled failure that can be achieved to minimize or eliminate the possibility harm to users of the devices or systems.

While the description above refers to particular embodiments of the present invention, it will be understood that many modifications may be made without departing from the spirit thereof The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A selectively protected electrical system for providing power from a power source to energize a load, comprising:
   a power driver circuit for controllably transferring power from the power source to the load, the power driver circuit being encapsulated; and
   a controller for enabling and disabling the power driver circuit, the controller being un encapsulated, such that contaminants in the protected electrical system are more likely to induce an electrical fault and disable the un-encapsulated controller and are substantially inhibited from inducing an electrical fault in the encapsulated power driver circuit.

2. The system recited in claim 1, wherein the power driver circuit is encapsulated by a potting material.

3. The system recited in claim 1, further comprising at least one un-encapsulated circuit element dissolvable by the contaminant such that the system is disabled.

4. The system recited in claim 3, wherein the at least one circuit element interrupts power when dissolved such that the system is disabled.

5. The system recited in claim 3, wherein the at least one circuit element is located in at least one of the power driver circuit and the controller.

6. The system recited in claim 1, further comprising at least one un-encapsulated circuit element for sensing a contaminant and passing a signal to the controller when the contaminant is sensed such that the controller disables the system.

7. The system recited in claim 6, wherein the at least one circuit element comprises a humidity sensor.

8. The system recited in claim 7, wherein the humidity sensor, upon sensing the contaminant, passes a signal to the controller which causes the controller to disable the system.

9. The system recited in claim 6, wherein the at least one circuit element comprises a pair of electrically isolated conductive plates separated by a distance adapted for receiving a contaminant between the conductive plates such that the contaminant shorts the conductive plates to one another.

10. The system recited in claim 8, wherein the signal further causes the controller to initiate a user-perceptible alarm.

11. The system recited in claim 10, wherein the user-perceptible alarm comprises at least one of an audio signal, a displayed message, and a vibration.

12. The system recited in claim 1, wherein the disabled controller cannot be further operated until the controller is reset.

13. The system recited in claim 1, wherein the power driver circuit comprises an H-bridge configuration of switching elements.

14. The system recited in claim 1, wherein the controller comprises control electronics.

15. The system recited in claim 1, wherein the controller comprises at least one microprocessor.

16. The system recited in claim 1, wherein the contaminant is conductive.

17. The system recited in claim 1, wherein the contaminant is moisture.

18. The system recited in claim 1, wherein the electrical fault comprises a short circuit condition.

19. The system recited in claim 2, wherein the potting material is a moisture-resistant potting material.

20. The system recited in claim 19, wherein the moisture-resistant potting material is selected from the group consisting essentially of parylene, room temperature vulcanizing silicone elastomers (RTV's), silicone, epoxies, adhesives, and plastics.

21. A selectively protected electrical system, comprising:
    a power source;
    a load;
    a power driver circuit for controllably transferring power from the power source to the load, the power driver circuit being encapsulated; and
    a controller for enabling and disabling the power driver circuit, the controller being un-encapsulated, such that a contaminant that may be in the system is more likely to induce an electrical fault and disable the un-encapsulated controller and is inhibited from inducing the electrical fault in the encapsulated power driver circuit.

22. The system recited in claim 21, wherein the load is a DC motor.

23. The system recited in claim 22, wherein the DC motor is used to drive a pump to deliver a fluid.

24. The system recited in claim 23, wherein the pump is an infusion pump, and wherein disabling the controller reduces the possibility of accidental delivery of excess fluid.

25. A power delivery system for safely providing power from a power source to energize a load, the system comprising:
    a control portion comprising a controller for controlling a power driver circuit;
    a power driver portion comprising the power driver circuit responsive to the controller for controllably transferring power from the power source to the load; and
    a potting material selectively covering the power driver portion such that the power driver circuit is encapsulated by the potting material and such that the control portion remains un-encapsulated by the potting material, and such that contaminants that may be in the system are more likely to induce an electrical fault and disable the un-encapsulated control portion and are inhibited from inducing the electrical fault in the encapsulated power driver circuit.

26. The system recited in claim 25, wherein the power driver circuit comprises an H-bridge configuration of switching elements.

27. The system recited in claim 25, wherein the controller comprises control electronics.

28. The system recited in claim 25, wherein the controller comprises at least one microprocessor.

29. The system recited in claim 25, further comprising a safety circuit coupled to the controller and the power driver portion and controlled by the controller to inhibit transferring power from the power source to the load when the safety circuit is in a disable state and to permit transferring power from the power source to the load when the safety circuit is in an enable state.

30. The system recited in claim 29 wherein the safety circuit is co-located with the controller.

31. The system recited in claim 29, wherein the safety circuit is integral with the load.

32. The system recited in claim 31, wherein the safety circuit is encapsulated by the potting material.

33. The system recited in claim 25, wherein the electrical fault comprises a short circuit condition.

34. The system recited in claim 25, wherein the potting material is a moisture-resistant potting material.

35. The system recited in claim 34, wherein the moisture-resistant potting material is selected from the group consisting essentially of parylene, room temperature vulcanizing silicone elastomers (RTV's), silicone, epoxies, adhesives, and plastics.

36. In an electrical system subject to contaminant exposure, a method for reducing the likelihood of a contamination induced electrical fault in a selected portion of the electrical system, the method comprising:
providing a critical portion of the electrical system for performing a critical operation;
providing a non-critical portion of the electrical system for enabling the critical portion to perform the critical operation; and
encapsulating the critical portion to provide a barrier between the critical portion and a contaminant such that the non-critical portion is un-encapsulated and such that a contaminant that may be in the system is more likely to induce an electrical fault in the un-encapsulated non-critical portion such that the non-critical portion disables the critical portion and such that the contaminant is inhibited from inducing the electrical fault in the encapsulated critical portion.

37. The method recited in claim 36, wherein encapsulating the critical portion comprises potting the critical portion with a moisture-resistant potting material.

38. The method recited in claim 37, wherein the moisture-resistant potting material is selected from the group consisting essentially of parylene, room temperature vulcanizing silicone elastomers (RTV's), silicone, epoxies, adhesives, and plastics.

39. In an electrical system subject to contaminant exposure, a method for reducing the likelihood of a contamination induced electrical fault in a selected portion of the electrical system, the method comprising:
providing a critical portion of the electrical system for performing a critical operation;
providing at least one circuit element operative to disable the electrical system when exposed to a contaminant; and
encapsulating the critical portion such that the at least one circuit element remains un-encapsulated and such that if the electrical system is exposed to the contaminant, the contaminant is more likely to contact the at least one un-encapsulated circuit element and disable the electrical system, and is inhibited from contacting the encapsulated critical portion.

40. The method recited in claim 39, wherein the at least one circuit element is dissolvable by the contaminant, such that exposure of the at least one circuit element to the contaminant dissolves the at least one circuit element and disables the electrical system.

41. The method recited in claim 39, wherein the at least one circuit element is a fuse.

42. The method recited in claim 39, wherein the at least one circuit element senses a contaminant, and wherein the at least one circuit element is operative to disable the electrical system when the contaminant is sensed.

43. The system recited in claim 42, wherein the at least one circuit element comprises a humidity sensor.

44. In an electrical system having a plurality of current paths subject to contaminant induced short circuiting, a method for protecting selected current paths, the method comprising:
providing at least one critical current path having at least one critical component for performing a critical operation;
providing at least one non-critical current path having at least one non-critical component for enabling the critical component to perform the critical operation;
encapsulating the at least one critical current path to provide a barrier between the at least one critical current path and a contaminant such that the at least one non-critical current path remains un-encapsulated and such that a short circuit is more likely to occur in the at least one un-encapsulated non-critical current path and to disable the electrical system and is inhibited from occurring in the at least one encapsulated critical current path.

45. The system recited in claim 1, wherein the disabled controller cannot be enabled.

46. The system recited in claim 1, wherein the electrical fault comprises an open circuit condition.

47. The system recited in claim 21, wherein the load is a sensor.

48. The system recited in claim 21, wherein the load is a sensor monitor.

49. The system recited in claim 21, wherein the load is a sensor meter.

50. The system recited in claim 21, wherein the load is a medical device.

51. The system recited in claim 21, wherein the load is a processor in a personal digital assistant (PDA).

52. A selectively protected electrical system, comprising:
a power source for providing power to an electrical circuit;
a power driver circuit for controllably transferring power from the power source to the electrical circuit, the power driver circuit being encapsulated; and
a controller for enabling and disabling the power driver circuit;
wherein the power source being un-encapsulated, such that contaminants in the protected electrical system are more likely to induce an electrical fault and disable the un-encapsulated power source and are substantially inhibited from inducing an electrical fault in the encapsulated power driver circuit.

53. The system recited in claim 52, wherein the power driver circuit is encapsulated by a potting material.

54. A selectively protected electrical system, comprising:
a power source for providing power to an electrical circuit;
a power driver circuit for controllably transferring power from the power source to the electrical circuit; and
a controller for enabling and disabling the power driver circuit, the controller being encapsulated;
wherein the power source being un-encapsulated, such that contaminants in the protected electrical system are more likely to induce an electrical fault and disable the un-encapsulated power source and are substantially inhibited from inducing an electrical fault in the encapsulated controller.

55. The system recited in claim 54, wherein the controller is encapsulated by a potting material.

56. The system recited in claim 54, wherein the power driver circuit is also encapsulated.

57. The system recited in claim 56, wherein the power driver circuit and the controller are encapsulated by a potting material.

58. A selectively protected electrical system, comprising:
a critical portion of the electrical system for performing a critical operation;
a non-critical portion of the electrical system for enabling the critical portion to perform the critical operation; and
wherein the critical portion is encapsulated to provide a barrier between the critical portion and a contaminant,
wherein the non-critical portion is un-encapsulated,
wherein a contaminant in the system is more likely to induce an electrical fault in the un-encapsulated non-critical portion such that the non-critical portion disables the critical portion and the contaminant is substantially inhibited from inducing the electrical fault in the encapsulated critical portion.

59. The system recited in claim 58, wherein the critical portion is encapsulated in a potting material.

60. The system recited in claim 59, wherein the potting material is moisture resistant potting material.

61. The system recited in claim 3, wherein the at least one circuit element is a fuse.

62. The system recited in claim 1, wherein the contaminant is ionic.

* * * * *